(12) United States Patent
Tipping

(10) Patent No.: US 11,185,423 B2
(45) Date of Patent: Nov. 30, 2021

(54) HIGHLY RADIOGRAPHICALLY OPAQUE METAL BASED INTERBODY

(71) Applicant: OSSEUS FUSION SYSTEMS, Dallas, TX (US)

(72) Inventor: Chase D. Tipping, Dallas, TX (US)

( * ) Notice: Subject to any disclaimer, the term of this patent is extended or adjusted under 35 U.S.C. 154(b) by 0 days.

(21) Appl. No.: 16/244,093

(22) Filed: Jan. 9, 2019

(65) Prior Publication Data
US 2020/0214852 A1  Jul. 9, 2020

(51) Int. Cl.
*A61F 2/44* (2006.01)
*A61F 2/30* (2006.01)

(52) U.S. Cl.
CPC .... *A61F 2/4465* (2013.01); *A61F 2002/3008* (2013.01); *A61F 2002/30011* (2013.01); *A61F 2002/3093* (2013.01); *A61F 2310/00023* (2013.01)

(58) Field of Classification Search
CPC .................................................. A61F 2/44–447
See application file for complete search history.

(56) References Cited

U.S. PATENT DOCUMENTS

| | | |
|---|---|---|
| D623,749 S | 9/2010 | Horton et al. |
| 8,142,886 B2 | 3/2012 | Noble et al. |
| 8,430,930 B2 | 4/2013 | Hunt |
| 9,271,845 B2 | 3/2016 | Hunt et al. |
| 9,421,108 B2 | 8/2016 | Hunt |
| 9,545,317 B2 | 1/2017 | Hunt |
| 9,549,823 B2 | 1/2017 | Hunt et al. |
| 9,572,669 B2 | 2/2017 | Hunt et al. |
| 2002/0099376 A1* | 7/2002 | Michelson ............ A61F 2/4455 606/86 A |
| 2005/0112397 A1* | 5/2005 | Rolfe ................ A61B 17/8605 428/593 |
| 2011/0082551 A1* | 4/2011 | Kraus ................... A61F 2/3601 623/17.11 |
| 2011/0224796 A1 | 9/2011 | Weiland et al. |
| 2011/0301709 A1* | 12/2011 | Kraus ................... A61F 2/4465 623/17.11 |
| 2013/0116793 A1* | 5/2013 | Kloss ..................... A61F 2/442 623/17.16 |
| 2016/0022431 A1* | 1/2016 | Wickham ................ A61F 2/447 623/17.16 |
| 2016/0074166 A1 | 3/2016 | Coale et al. |
| 2016/0193055 A1 | 7/2016 | Ries |
| 2016/0213485 A1 | 7/2016 | Schaufler et al. |
| 2016/0213486 A1 | 7/2016 | Nunley et al. |
| 2016/0213487 A1* | 7/2016 | Wilson .................. A61F 2/4465 |
| 2016/0213488 A1* | 7/2016 | Moore .................. A61F 2/4465 |

(Continued)

FOREIGN PATENT DOCUMENTS

| | | |
|---|---|---|
| WO | 2008/082766 A2 | 7/2008 |
| WO | 2012/112702 A2 | 8/2012 |

(Continued)

*Primary Examiner* — Eduardo C Robert
*Assistant Examiner* — Steven J Cotroneo
(74) *Attorney, Agent, or Firm* — Merle W. Richman, III

(57) ABSTRACT

Embodiments of bony region interbody systems, apparatus, and methods are described generally herein including a spinal interbody for insertion between vertebra, the interbody formed of metals or alloys while providing high radiographic visibility. Other embodiments may be described and claimed.

20 Claims, 26 Drawing Sheets

(56) References Cited

U.S. PATENT DOCUMENTS

2016/0324653 A1 11/2016 Flickinger et al.
2016/0331546 A1 11/2016 Lechmann et al.

FOREIGN PATENT DOCUMENTS

| WO | 2014/145567 A1 | 9/2014 |
| WO | 2016/130878 A1 | 8/2016 |
| WO | 2016/179555 A1 | 11/2016 |
| WO | 2017/009242 A1 | 1/2017 |

* cited by examiner

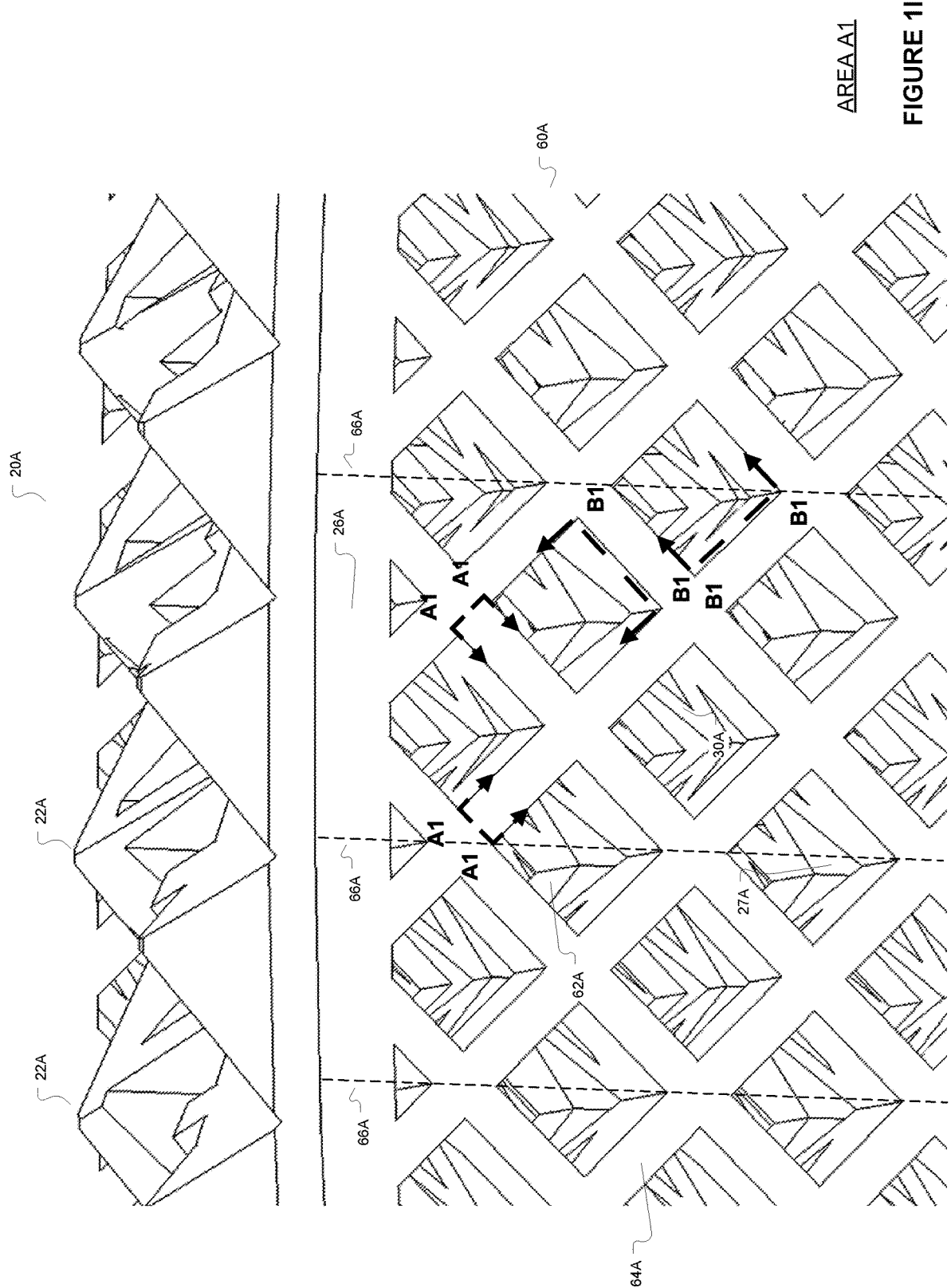

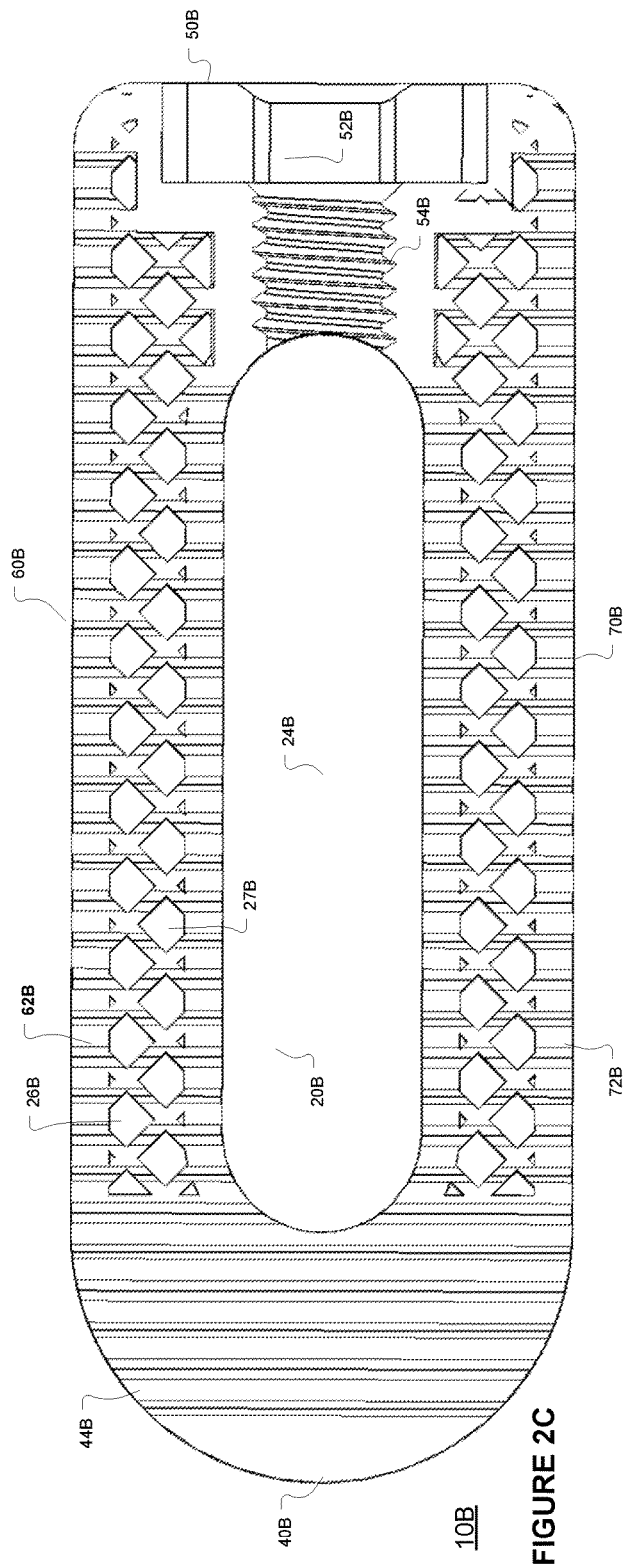
FIGURE 2C
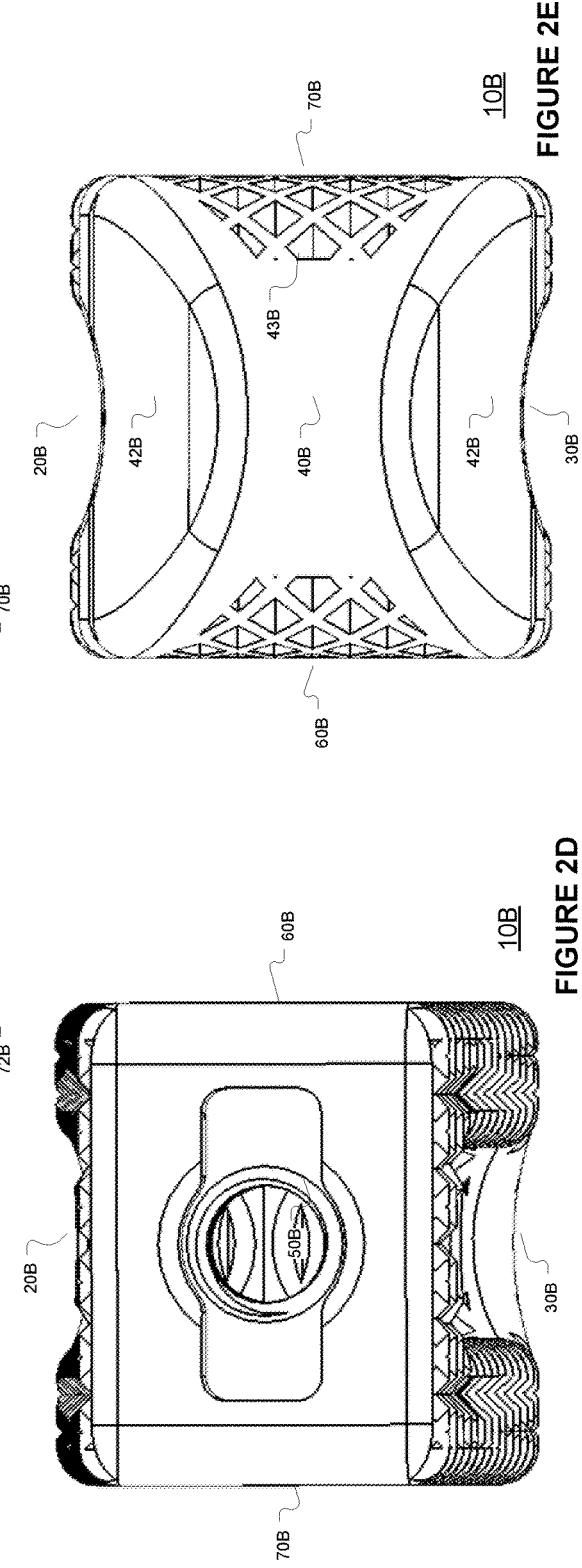
FIGURE 2D
FIGURE 2E

AREA A2

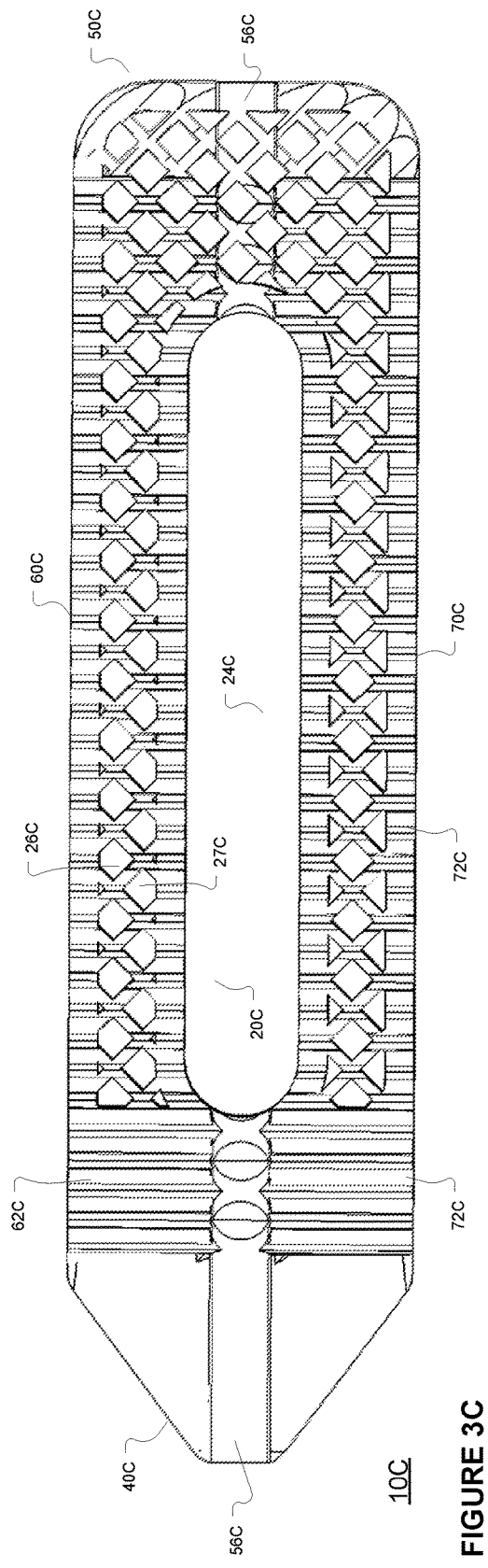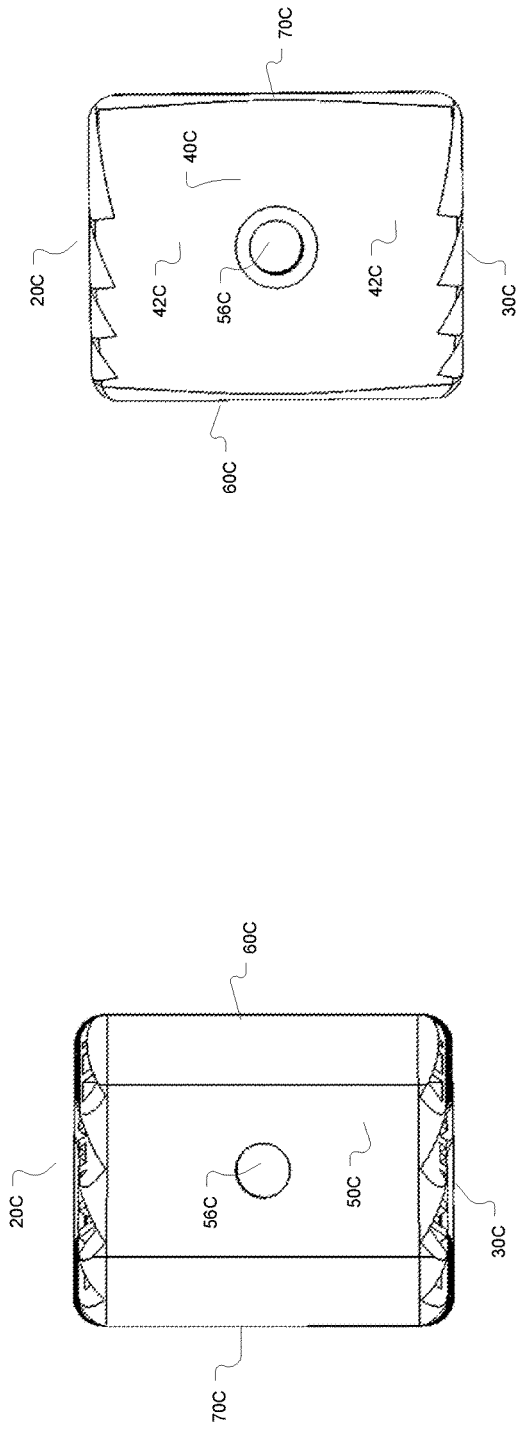
FIGURE 3C
FIGURE 3D
FIGURE 3E

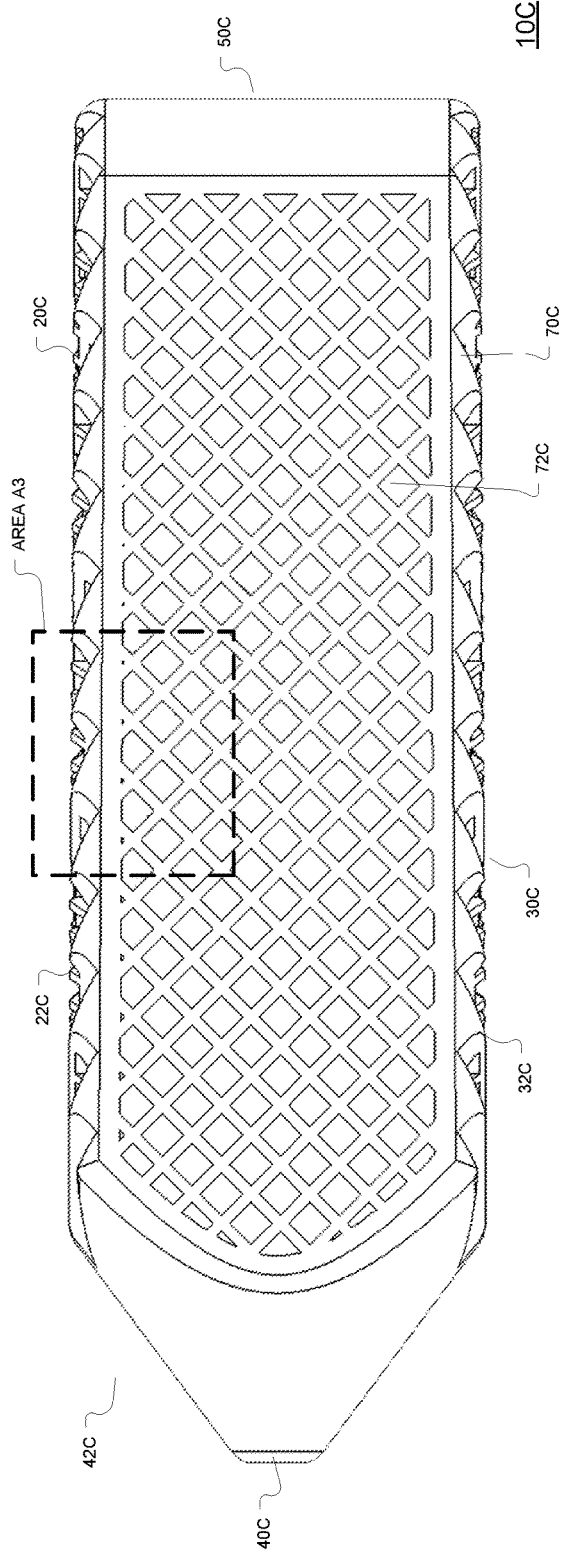
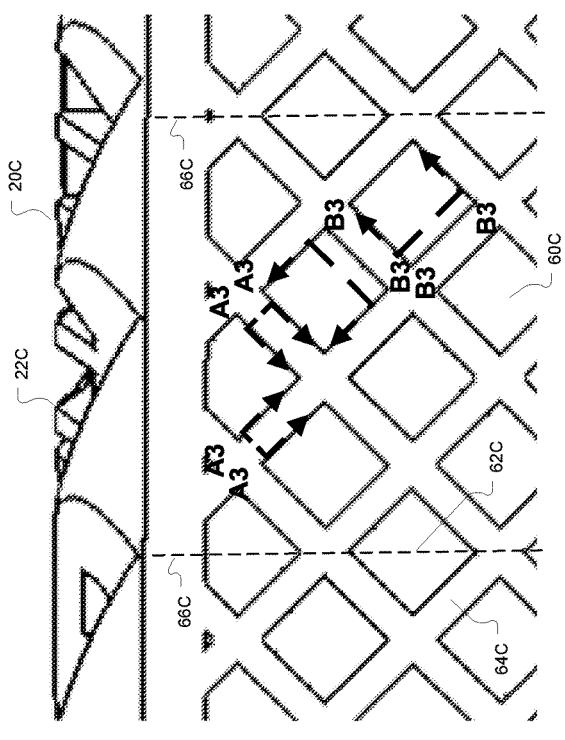
FIGURE 3F
AREA A3
FIGURE 3G

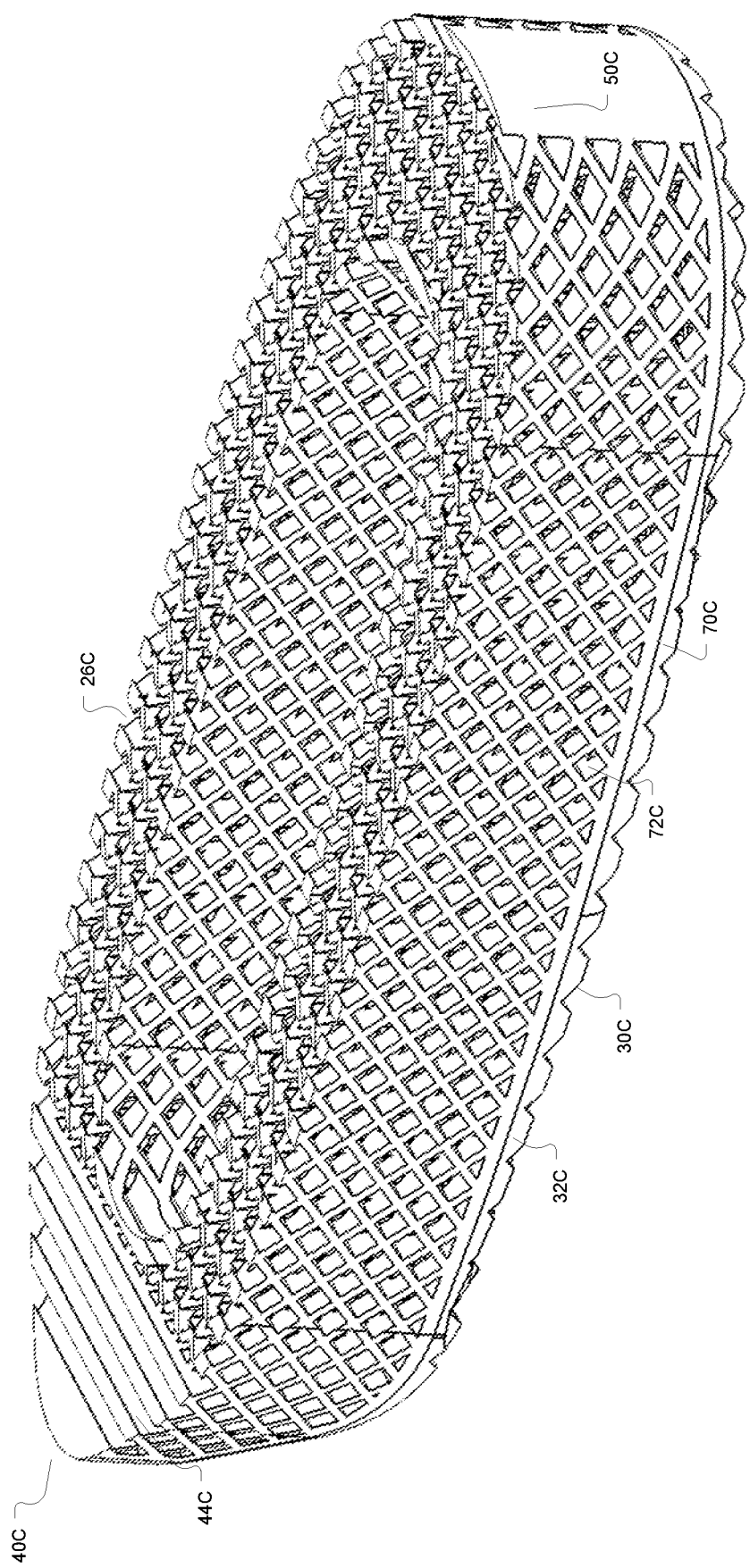

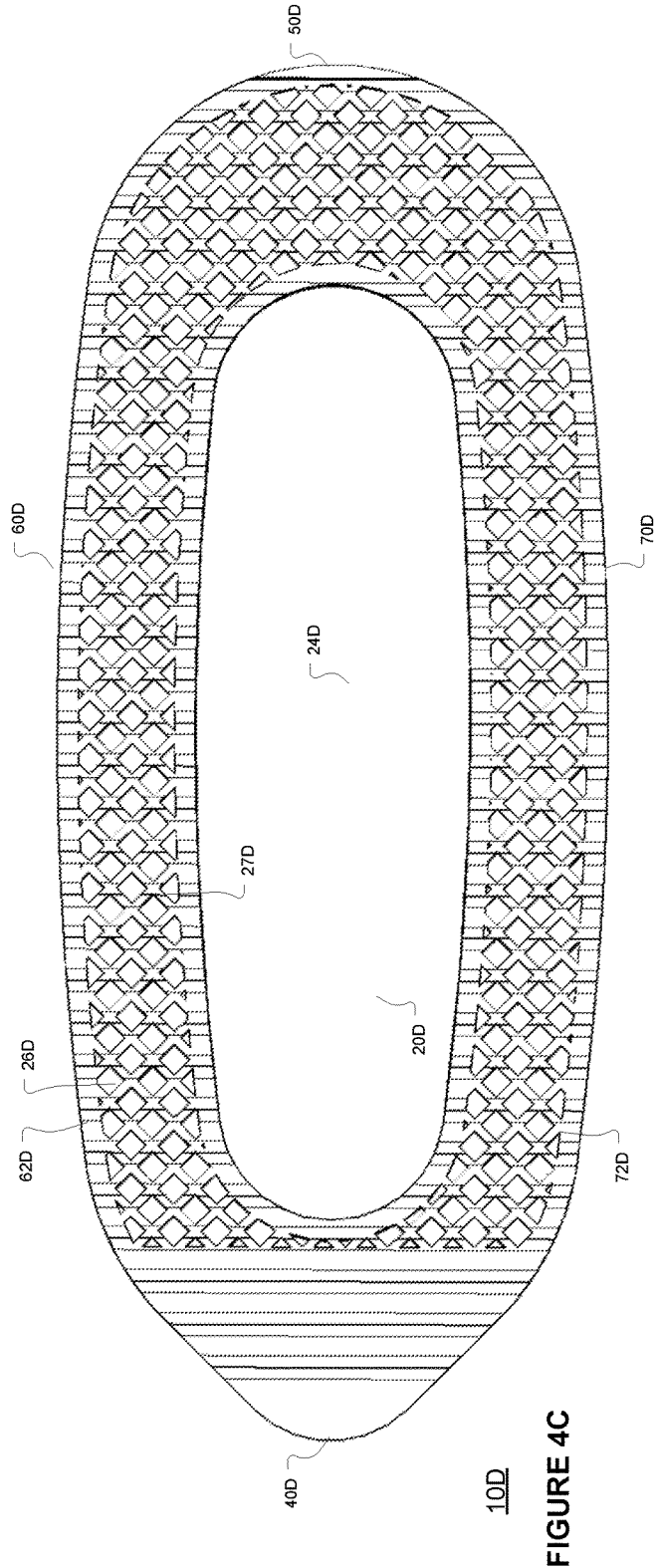
FIGURE 4C
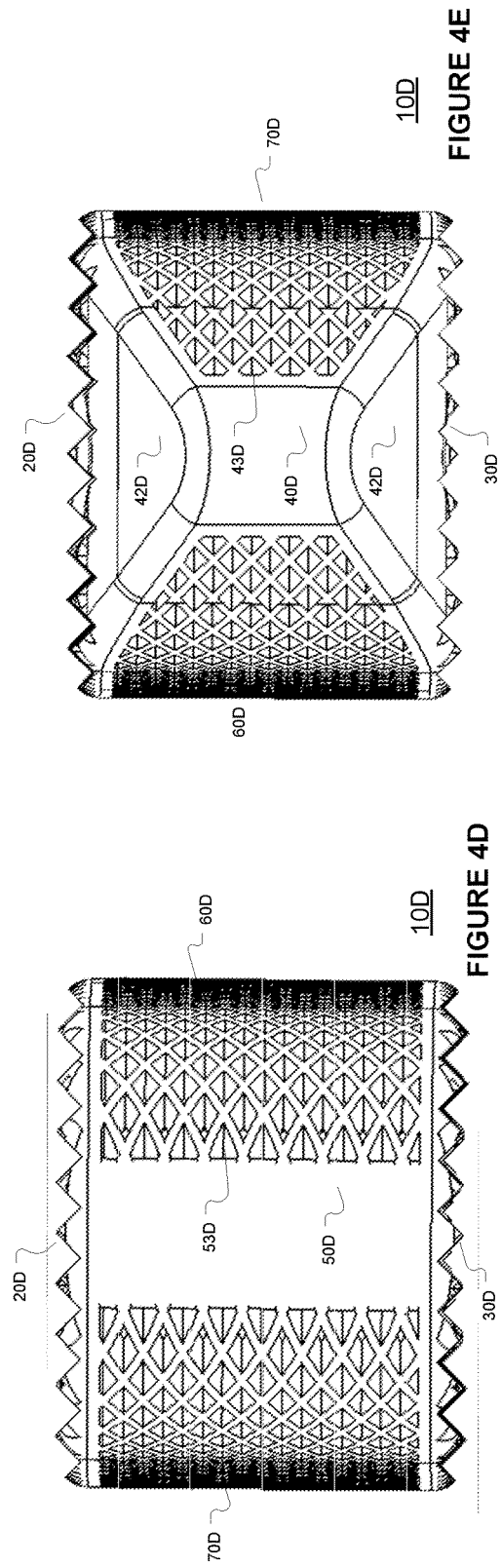
FIGURE 4D
FIGURE 4E

AREA A4

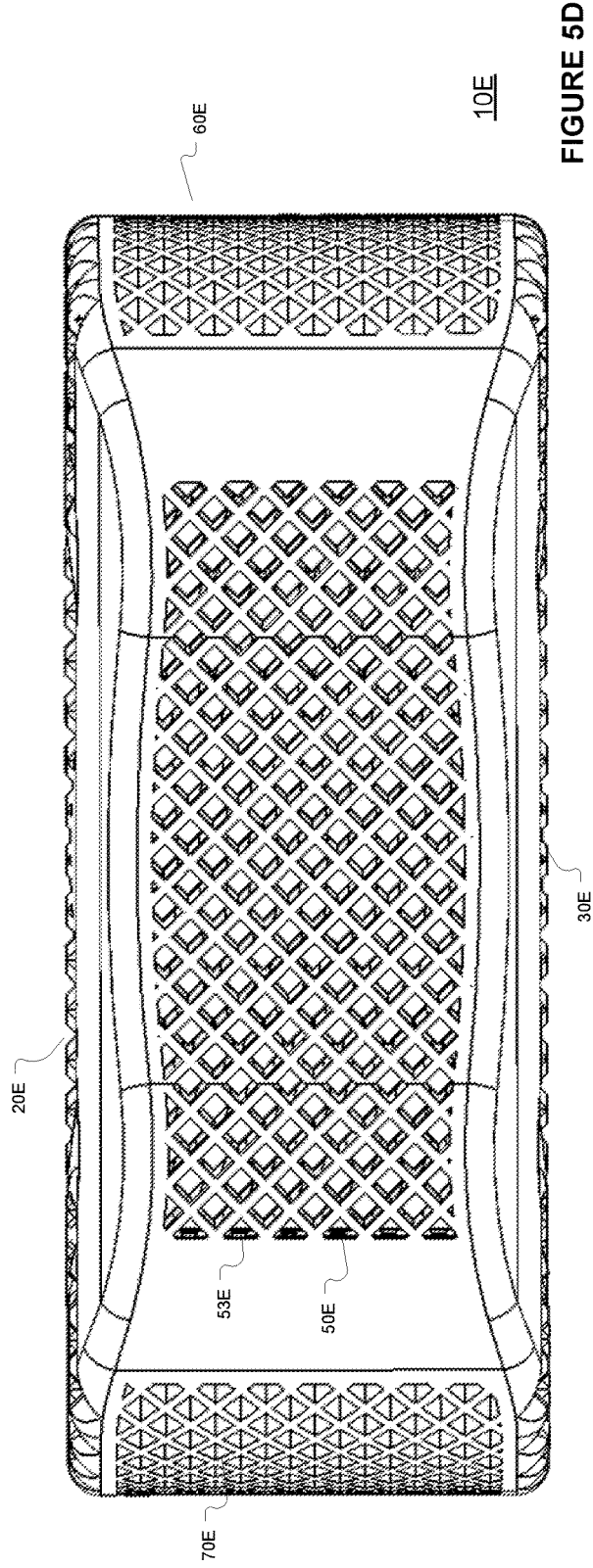
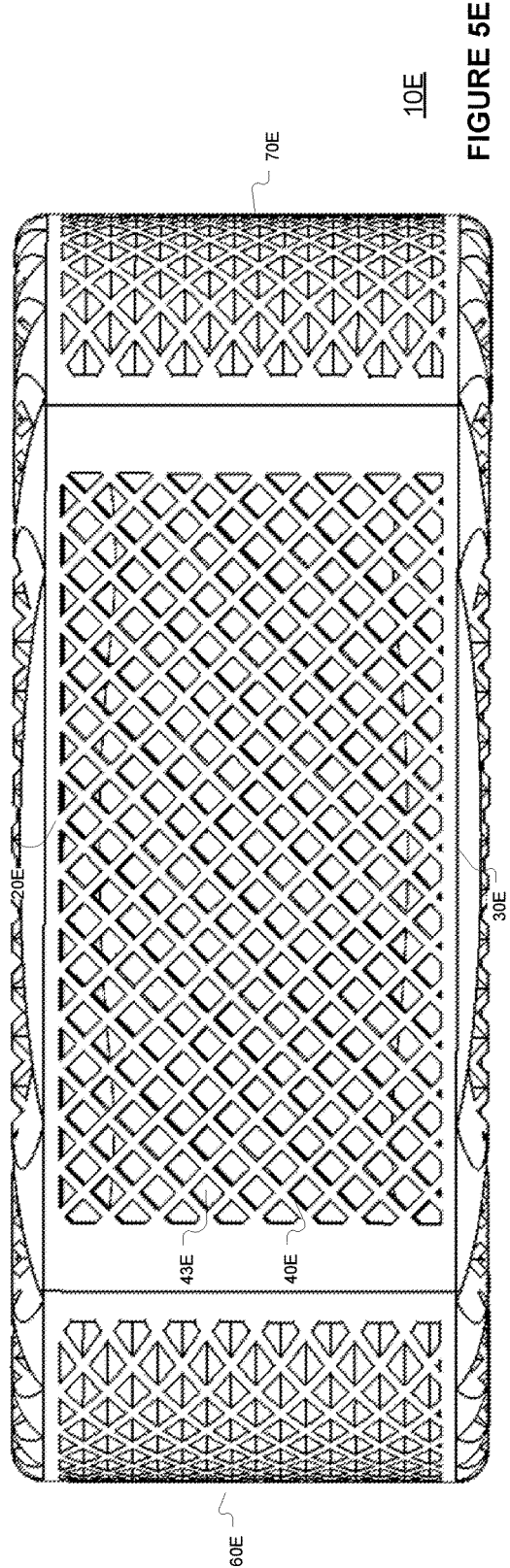
FIGURE 5D
FIGURE 5E

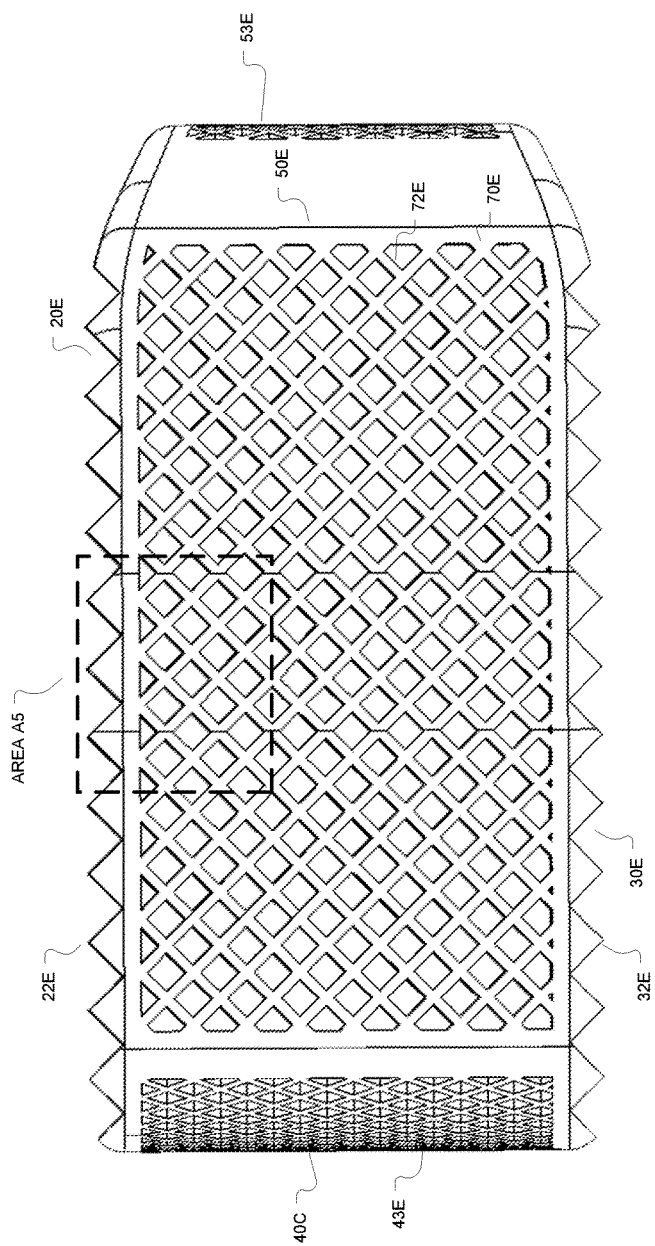
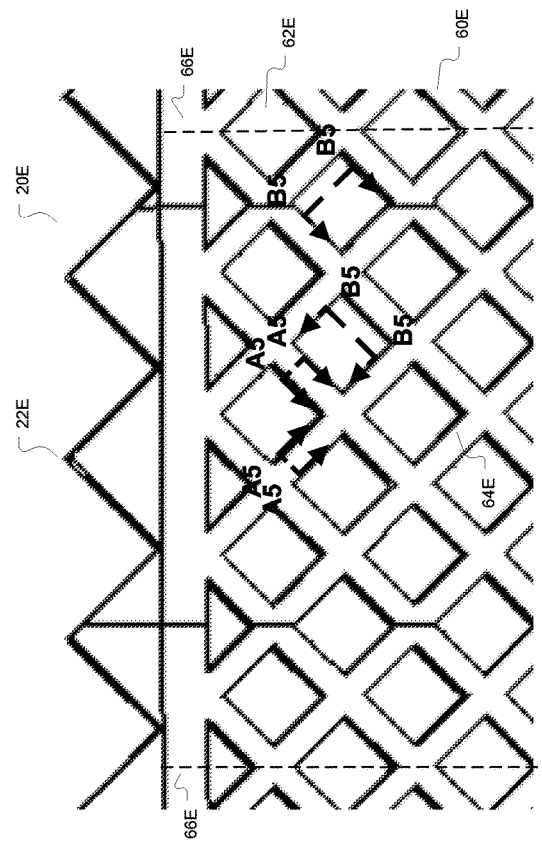
FIGURE 5F
AREA A5
FIGURE 5G

HIGHLY RADIOGRAPHICALLY OPAQUE METAL BASED INTERBODY

TECHNICAL FIELD

Various embodiments described herein relate generally to stabilizing mammalian bony segments, including systems and methods to employ an interbody sized to be inserted or implanted between mammalian bony segments to be stabilized or fused.

BACKGROUND INFORMATION

It may be desirable to stabilize or cause bony fusion between adjacent bony segments via interbod(ies) to be inserted between the adjacent bony segments, the present invention provides methods, systems, and apparatus for such treatment and deploying such treatment.

BRIEF DESCRIPTION OF THE DRAWINGS

FIG. 1I is a simplified right-side view of area A1 of the bony interbody apparatus shown in FIG. 1A according to various embodiments.

FIG. 2C is a simplified, X-Y cross-sectional top view of the bony interbody apparatus shown in FIG. 2A according to various embodiments.

FIG. 2D is a simplified, back view of the bony interbody apparatus shown in FIG. 2A according to various embodiments.

FIG. 2E is a simplified, front view of the bony interbody apparatus shown in FIG. 2A according to various embodiments.

FIG. 3C is a simplified, X-Y cross-sectional top view of the bony interbody apparatus shown in FIG. 3A according to various embodiments.

FIG. 3D is a simplified, back view of the bony interbody apparatus shown in FIG. 3A according to various embodiments.

FIG. 3E is a simplified, front view of the bony interbody apparatus shown in FIG. 3A according to various embodiments.

FIG. 3F is a simplified, left-side view of the bony interbody apparatus shown in FIG. 3A according to various embodiments.

FIG. 3G is a simplified left-side view of area A3 of the bony interbody apparatus shown in FIG. 3F according to various embodiments.

FIG. 4B is a simplified, X-Y cross-sectional left-side view of the bony interbody apparatus shown in FIG. 4A according to various embodiments.

FIG. 4C is a simplified, X-Y cross-sectional top view of the bony interbody apparatus shown in FIG. 4A according to various embodiments.

FIG. 4D is a simplified, back view of the bony interbody apparatus shown in FIG. 4A according to various embodiments.

FIG. 4E is a simplified, front view of the bony interbody apparatus shown in FIG. 4A according to various embodiments.

FIG. 5D is a simplified, back view of the bony interbody apparatus shown in FIG. 5A according to various embodiments.

FIG. 5E is a simplified, front view of the bony interbody apparatus shown in FIG. 5A according to various embodiments.

FIG. 5F is a simplified, left-side view of the bony interbody apparatus shown in FIG. 5A according to various embodiments.

FIG. 5G is a simplified left-side view of area A5 of the bony interbody apparatus shown in FIG. 5F according to various embodiments.

DETAILED DESCRIPTION

It may be desirable to stabilized or fuse adjacent bony regions or segments 222 by implanting one or more interbody devices or apparatus 10A-10E. The bony regions 222 may be separated by one or more non-bony elements 224, for example the bony regions 222 may be vertebra separated by spinal discs 224 in a cervical, thoracic, or lumbar region of a mammal including a human. In another embodiment the bony regions 222 may be part of a single, fractured bone to be stabilized such a femur or other long mammalian bone.

Accordingly, the one or more interbody devices or apparatus 10A-10E should enable, support, or support bony growth between the adjacent bony regions 222 so fusion may occur. The one or more interbody devices or apparatus 10A-10E should also be substantially opaque when viewed by an imaging system so a medical professional may clearly note is location and see bony growth or fusion between the adjacent bony regions 222.

In particular, during implantation, a medical professional (such as a surgeon) may want to verify the location(s) of the one or more interbody devices or apparatus 10A-10E via an imaging system such as a radiographic system such as a C-arm, X-ray machine, or other instrument that generates and records imaging signals. A medical professional may also want to verify the location(s) of the one or more interbody devices or apparatus 10A-10E after surgery and during follow up visits via similar imaging systems. In addition, a medical professional may want to verify that adjacent regions 222 are fused or becoming fused via an imaging system.

Interbodies formed of a metal or metal alloy such as Titanium and others are substantially better bony fusion constructs than interbodies formed from non-metal or non-alloy materials such a polyether ether ketone (PEEK), ceramics, or others. Interbodies formed of a metal or metal alloy such as Titanium and others, however may be occlude images, making it difficult for a medical professional to verify their location relative to the bony regions 222 and bony growth or fusion.

The interbody apparatuses 10A-10E as shown in FIGS. 1A-8B are formed of a metal or metal alloy such as Titanium and others but include substantial horizontal and vertical fenestrations 26A-26E, 27A-27E, 43A-43E, 62A-62E, and 72A-72E that serve to two key functions: a) providing scaffolds for bony growth and b) providing pathways for imaging system signals. Such imaging system's signals pathways make the interbody apparatuses 10A-10E as shown in FIGS. 1A-8B substantially more opaque than an interbody without such fenestrations or openings. The interbody apparatuses 10A-10E embodiments are described in detail with reference to FIGS. 1A-8B.

Figure 1A:
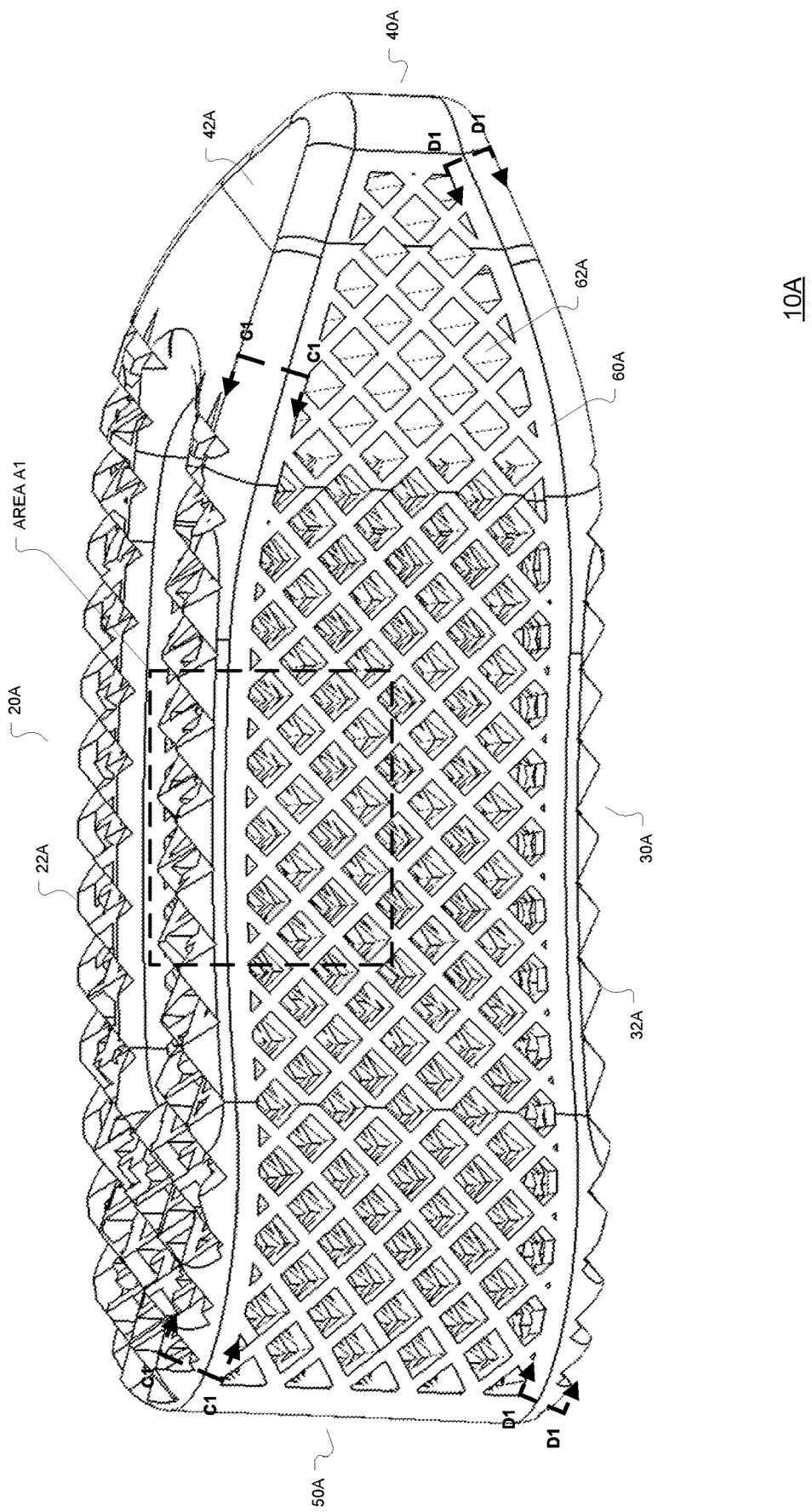
FIG. 1A is a simplified, isometric right-side view of a bony interbody apparatus according to various embodiments where the interbody may be a Transforaminal Curved Lumbar Interbody Fusion (TCLIF) interbody.
Figure 1B:
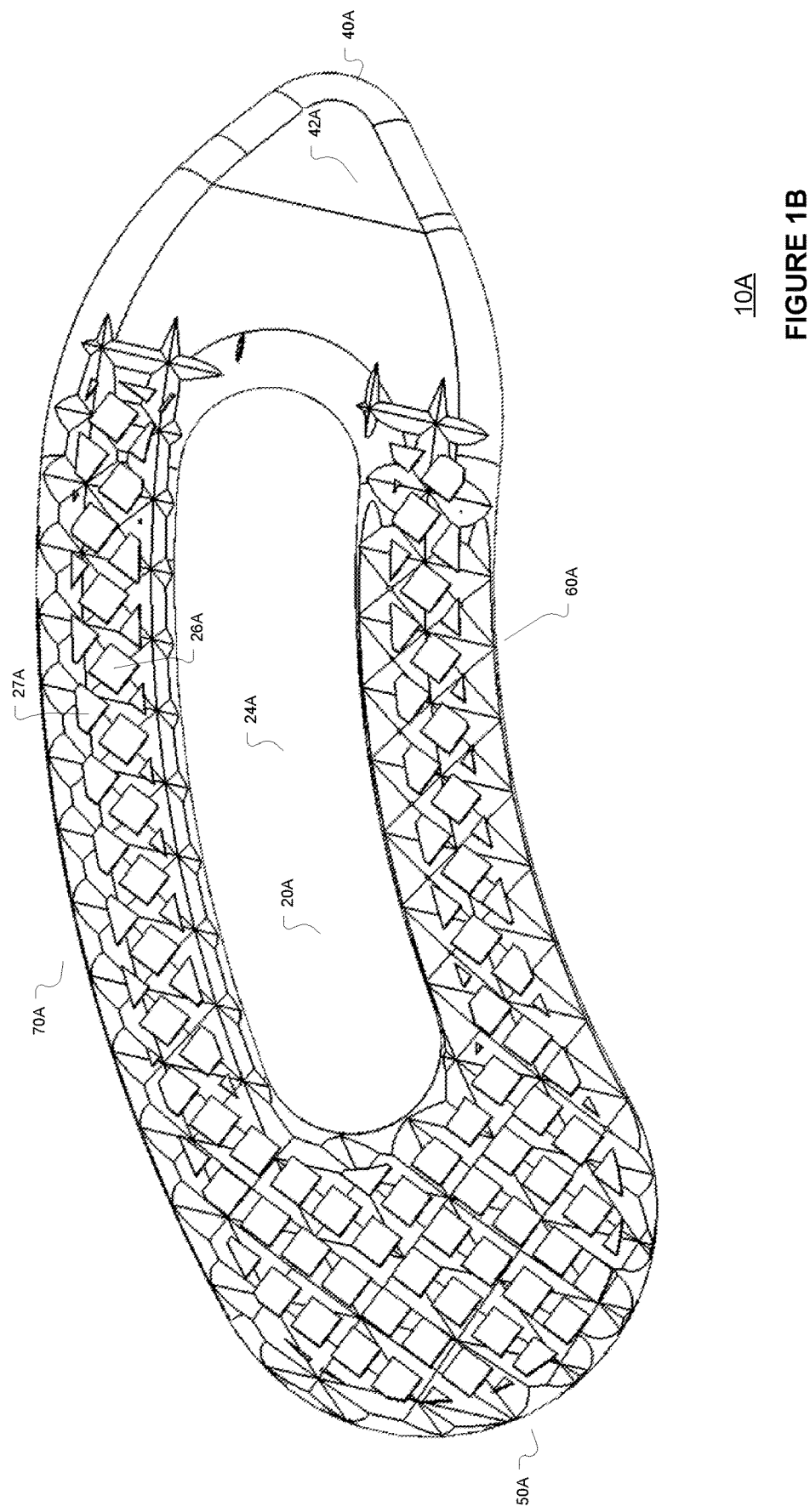
FIG. 1B is a simplified, top view of the bony interbody apparatus shown in FIG. 1A according to various embodiments.
Figure 1C:
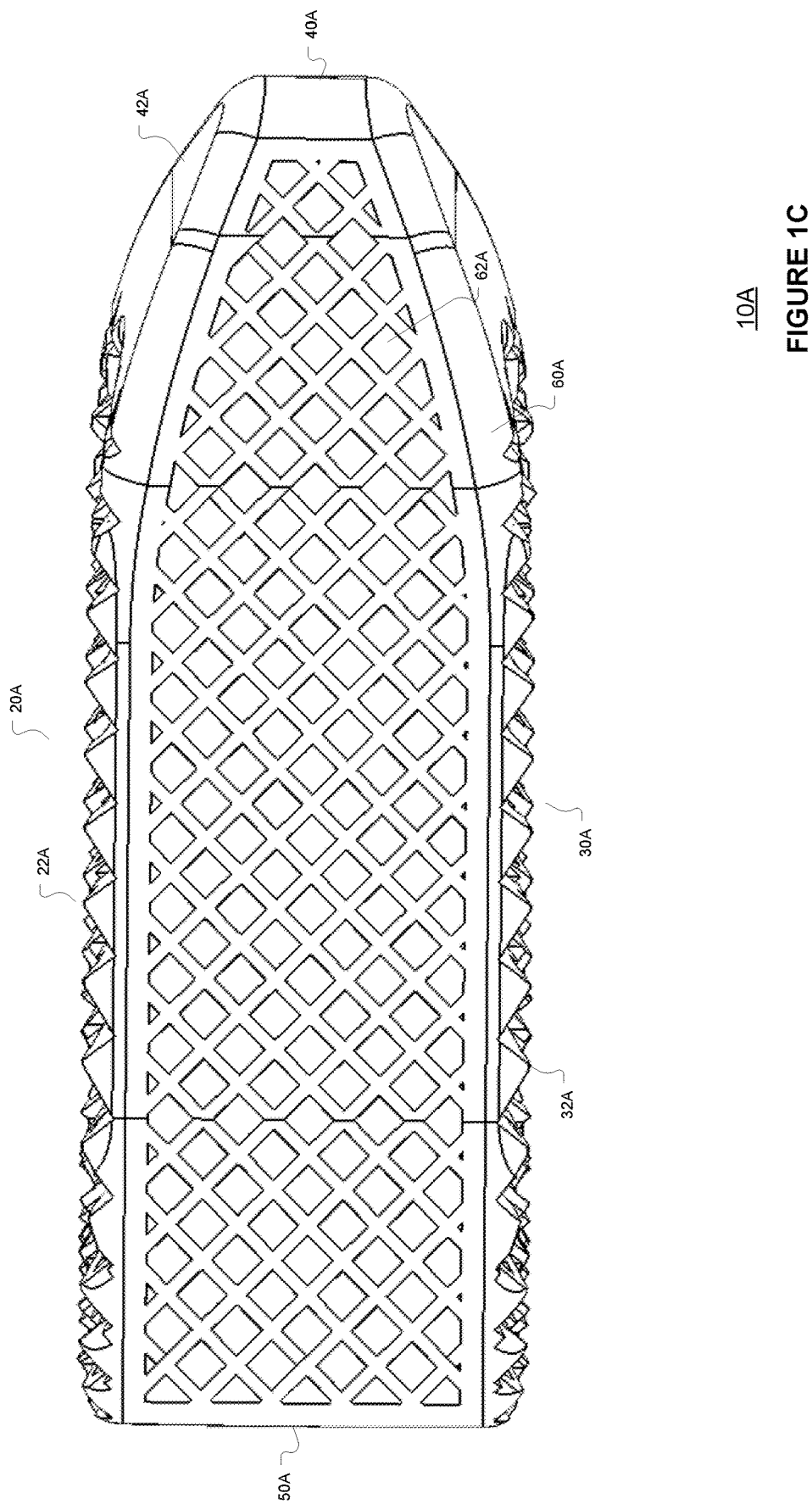
FIG. 1C is a simplified, right-side view of the bony interbody apparatus shown in FIG. 1A according to various embodiments.
Figure 1D:
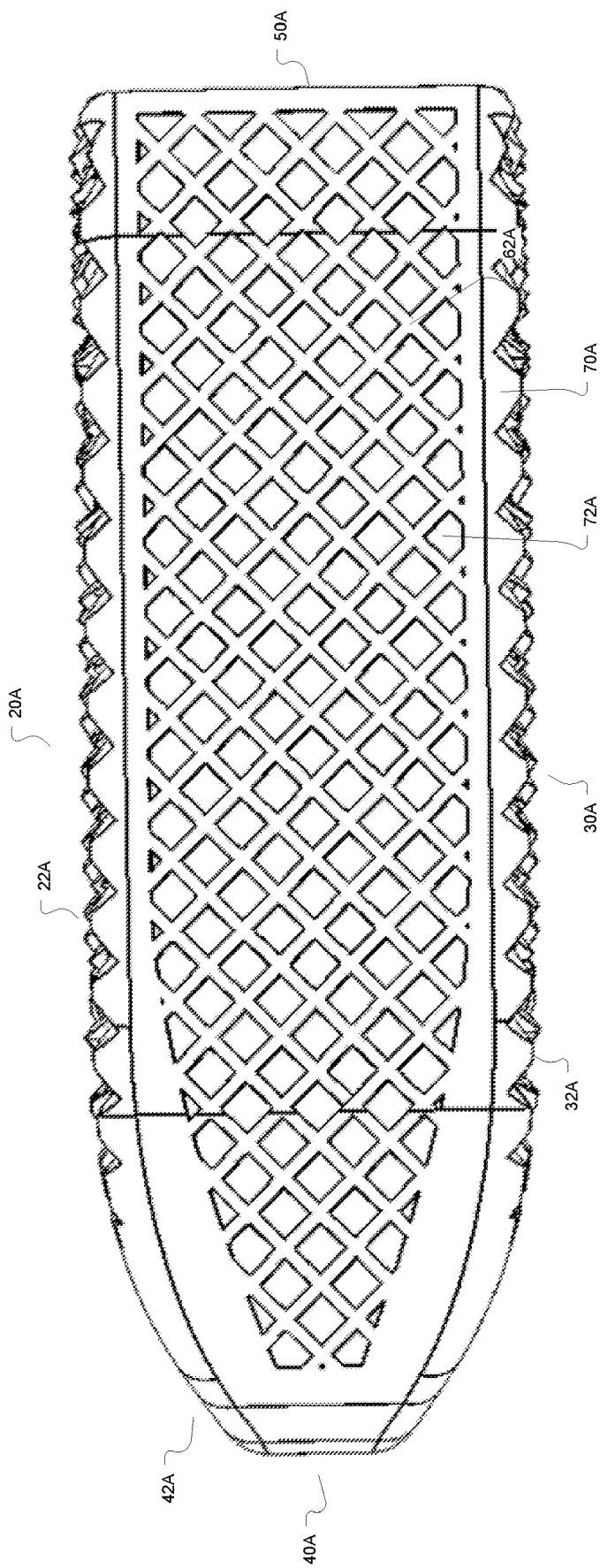
FIG. 1D is a simplified, left-side view of the bony interbody apparatus shown in FIG. 1A according to various embodiments.
Figure 1E:
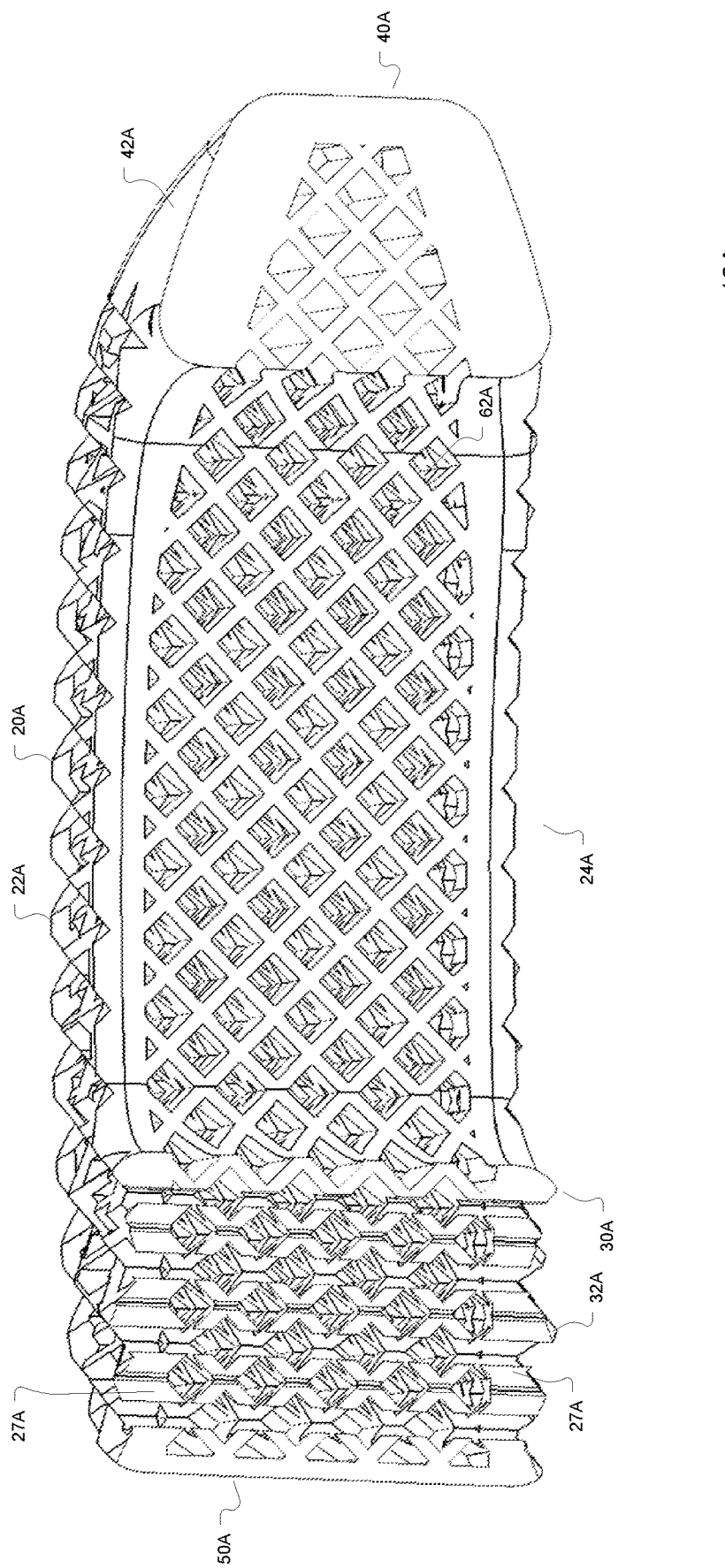
FIG. 1E is a simplified, X-Z cross-sectional right-side view of the bony interbody apparatus shown in FIG. 1A according to various embodiments.

FIG. 1A is a simplified, isometric right-side view of a bony interbody apparatus 10A according to various embodiments where the interbody apparatus 10A may be a Transforaminal Curved Lumbar Interbody Fusion (TCLIF) interbody apparatus 10A. FIG. 1B is a simplified, top view of the bony interbody apparatus 10A shown in FIG. 1A according to various embodiments. FIG. 1C is a simplified, right-side view of the bony interbody apparatus 10A shown in FIG. 1A according to various embodiments. FIG. 1D is a simplified, left-side view of the bony interbody apparatus 10A shown in FIG. 1A according to various embodiments. FIG. 1E is a simplified, X-Z cross-sectional right-side view of the bony interbody apparatus 10A shown in FIG. 1A according to various embodiments.

Figure 1F:
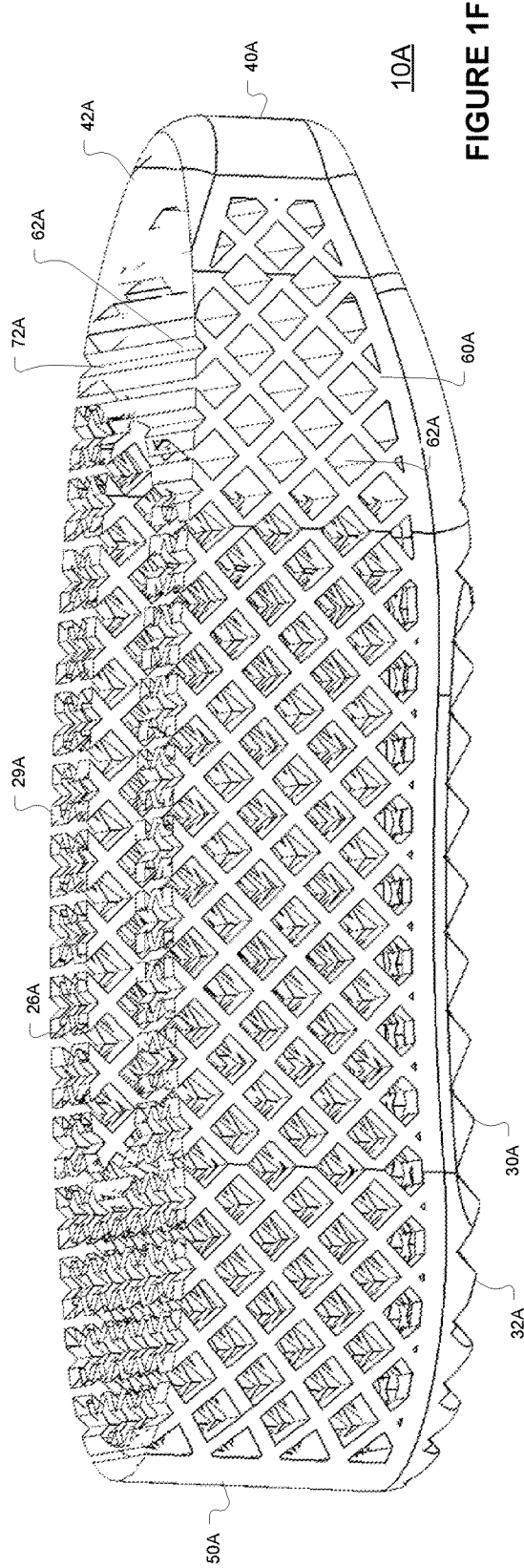
FIG. 1F is a simplified, X-Y cross-sectional right-side view of the bony interbody apparatus shown in FIG. 1A according to various embodiments.
Figure 1H:
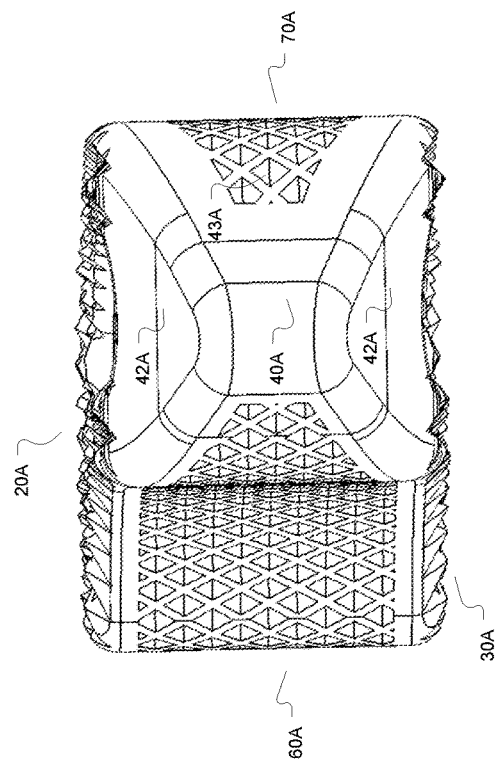
FIG. 1H is a simplified, front view of the bony interbody apparatus shown in FIG. 1A according to various embodiments.
Figure 1G:
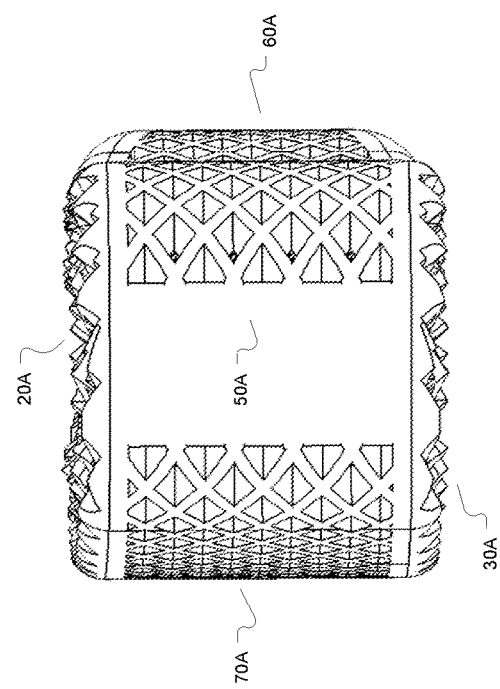
FIG. 1G is a simplified, back view of the bony interbody apparatus shown in FIG. 1A according to various embodiments.
Figure 1J:
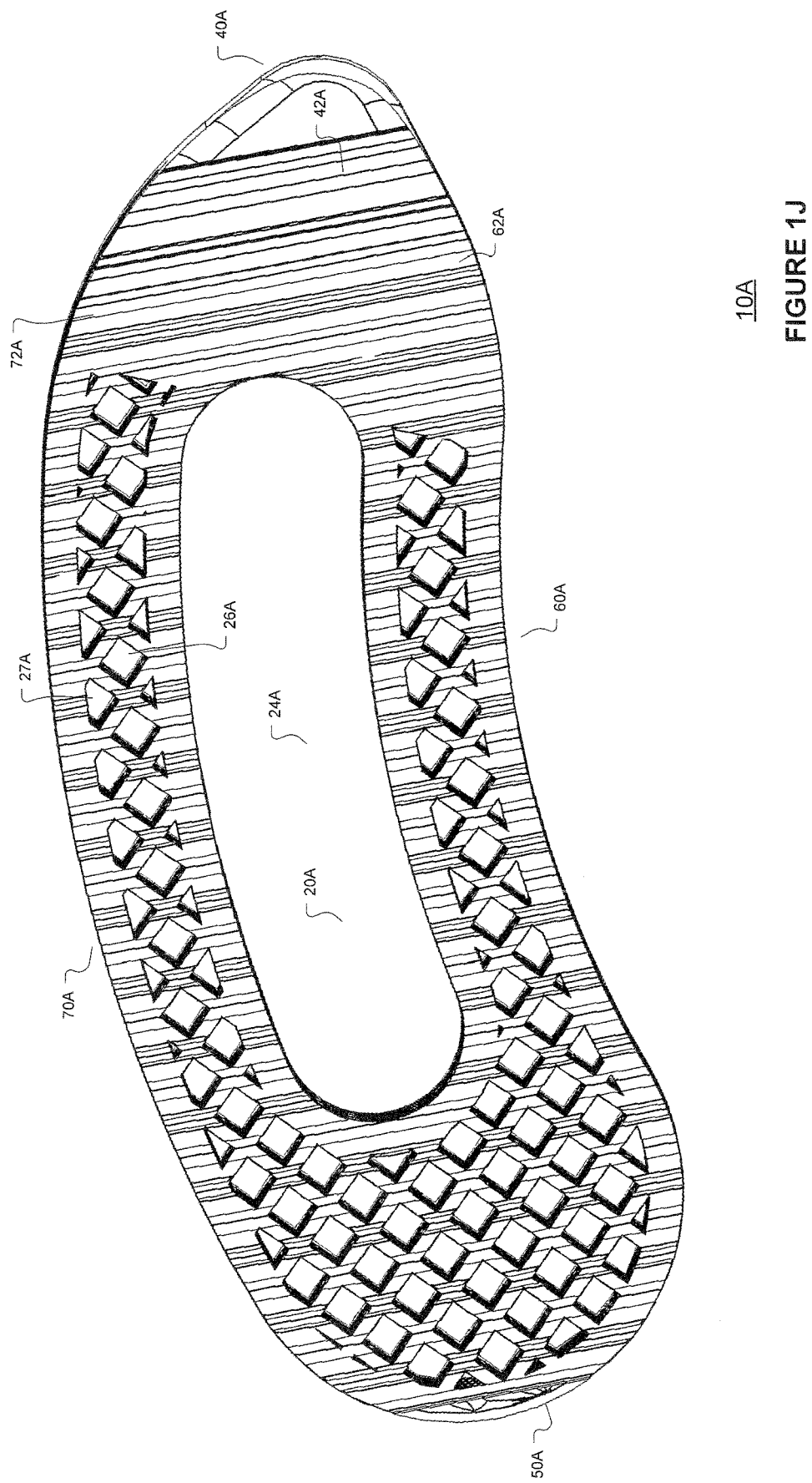
FIG. 1J is a simplified, X-Y cross-sectional top view of the bony interbody apparatus shown in FIG. 1A according to various embodiments.

FIG. 1F is a simplified, X-Y cross-sectional right-side view of the bony interbody apparatus 10A shown in FIG. 1A according to various embodiments. FIG. 1G is a simplified, back view of the bony interbody apparatus 10A shown in FIG. 1A according to various embodiments. FIG. 1H is a simplified, front view of the bony interbody apparatus 10A shown in FIG. 1A according to various embodiments. FIG. 1I is a simplified right-side view of area A1 of the bony interbody apparatus 10A shown in FIG. 1A according to various embodiments. FIG. 1J is a simplified, X-Y cross-sectional top view of the bony interbody apparatus 10A shown in FIG. 1A according to various embodiments.

As shown in FIGS. 1A-1J, the interbody apparatus 10A includes a top 20A, bottom 30A, front 40A, back 50A, right-side 60A, and left-side 70A. The apparatus 10A includes a large central fenestration 24A extending completely from the top 20A to the bottom 30A. The apparatus also includes fenestrations 62A that extend completely from its right-side 60A to the its left-side 70A matching fenestration 72A (complete channel). As shown in the FIGS. 1A-1I and in detail in FIG. 1I, side fenestrations 62A, 72A, may have walls 64A having a substantially uniform width A1-A1 that form the fenestrations 62A opening widths B1-B1. In an embodiment, the wall width A1-A1 may be about 0.15 to 0.5 mm and about 0.30 mm in an embodiment and the opening widths B1-B1 may be about 0.4 mm to 2.0 mm and about 0.80 mm in an embodiment.

As also shown in FIGS. 1A-1I and in particular in FIG. 1A, the apparatus 10A may have a substantially uniform upper surface and lower surface offset width C1-C1 and D1-D1 from the side fenestrations 62A, 72A. In an embodiment, the widths C1-C1 and D1-D1 may be about 0.5 mm to 3.0 mm and about 1.25 mm and 1.5 mm in an embodiment. It is noted that the apparatus 10A may a range of overall lengths of about 20 to 35 mm, widths of about 8 mm to 15 mm, and heights of about 7 mm to 20 mm depending on the patient anatomy.

This uniform offset C1-C1, D1-D1 width, wall widths A1-A1, and opening widths B1-B1 may enable the apparatus 10A to support the loads created between the bony regions 222 without failure. The apparatus 10A further includes fenestrations 26A, 27A in its formed teeth or protrusions 22A that form complete channels to its bottom 30A. These channels formed by the fenestrations 26A, 27A, 62A, 72A, as noted a) may prove scaffolds for bony growth and b) may provide pathways for imaging system signals.

The ratio of the wall width A1-A1 to the opening widths B1-B1 may be about 1:4 to 1:2 and about 3:8 in an embodiment. Further, a line 66A vertically bisecting the diamond pattern side fenestrations 62A may be oriented perpendicularly to the top and the bottom surfaces 20A, 30A to provide uniform load distribution even in embodiments that are sloped (for lordosis) as shown in FIGS. 2F and 2G. In an embodiment as shown FIGS. 1A-1I, the front 40A insertion area including the slanted surface 42A may be stronger than the adjacent section of the implant 10A. As shown in FIGS. 1A-1I, the implant 10A insertion area 42A may not include vertical fenestrations 27A or be part of the large central fenestration 24A. Further, the insertion area 42A may not include teeth or protrusions 22A easing the insertion resistance and further strengthening the insertion area 42A.

In an embodiment, the apparatus 10A-10E may be formed via a 3-D or additive printing process including direct metal laser sintering, 3D metal molding, electron beam additive manufacturing, electron beam welding, and electron beam melting. Similar techniques and geometrics may be applied to other shaped Interbodies for different applications including the Transforaminal curved lumbar interbody fusion (TCLIF) apparatus 10A shown in FIGS. 1A-1I, the Transforaminal straight lumbar interbody fusion (TSLIF) apparatus 10B shown in FIGS. 2A-2G, the Oblique Lumbar Interbody Fusion (OLIF) apparatus 10C shown in FIGS. 3A-3G, the Lateral Lumbar Interbody Fusion (LLIF) apparatus 10D shown in FIGS. 4A-4G, and the Anterior Lumbar Interbody Fusion (ALIF) apparatus 10E shown in FIGS. 5A-5G.

Figure 2A:
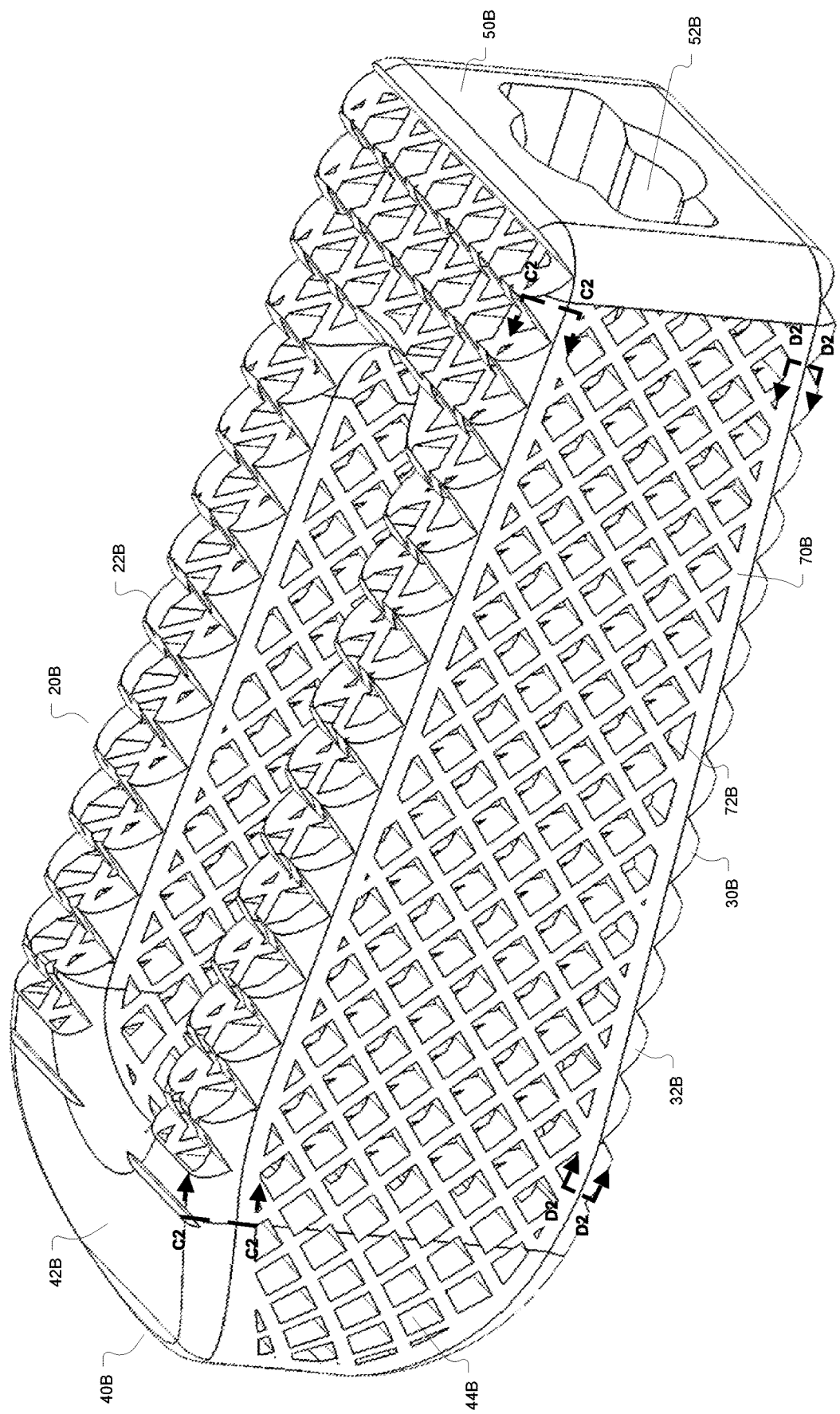
FIG. 2A is a simplified, isometric left-side view of a bony interbody apparatus according to various embodiments where the interbody may be a Transforaminal Straight Lumbar Interbody Fusion (TSLIF) interbody.
Figure 2B:
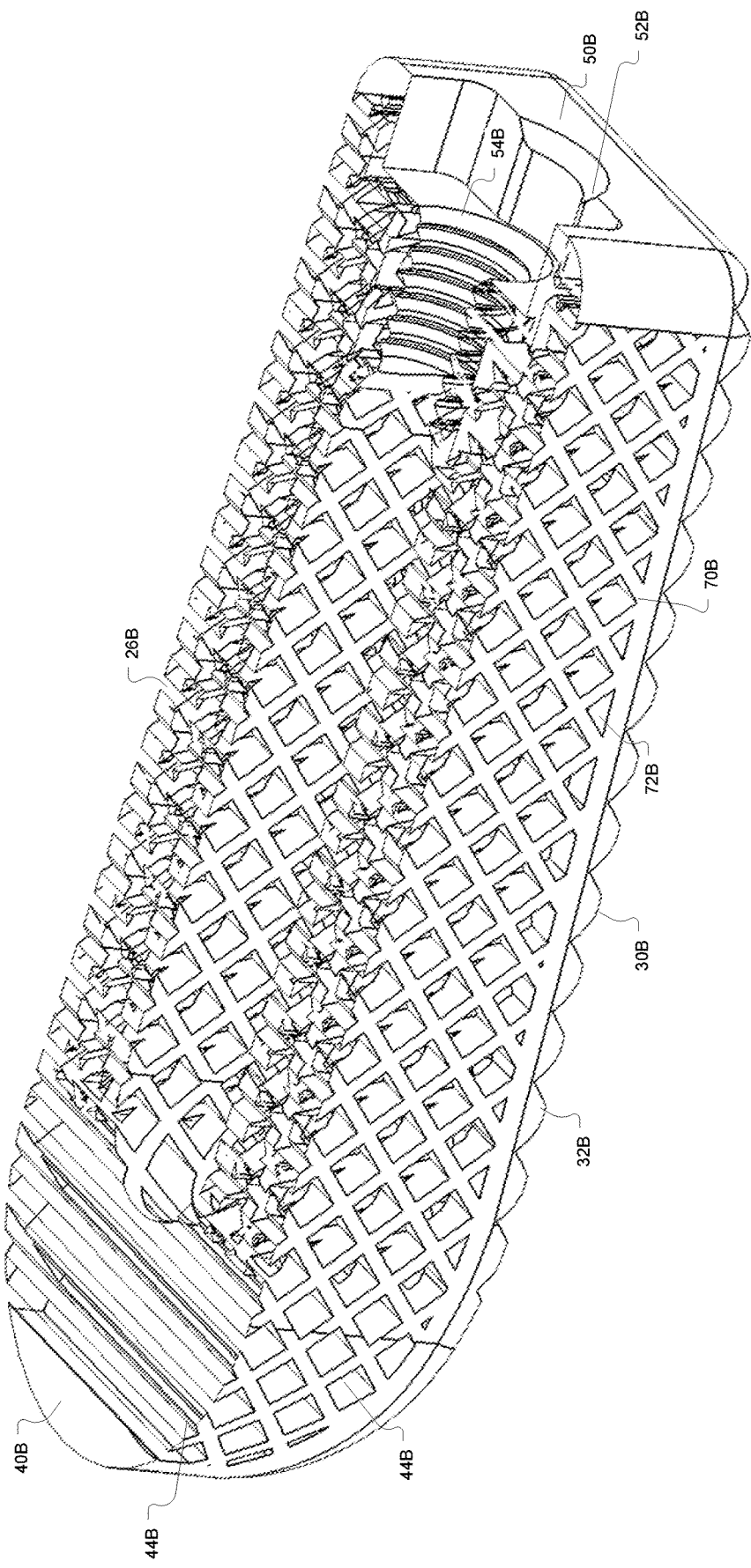
FIG. 2B is a simplified, X-Y cross-sectional left-side view of the bony interbody apparatus shown in FIG. 2A according to various embodiments.
Figure 2F:
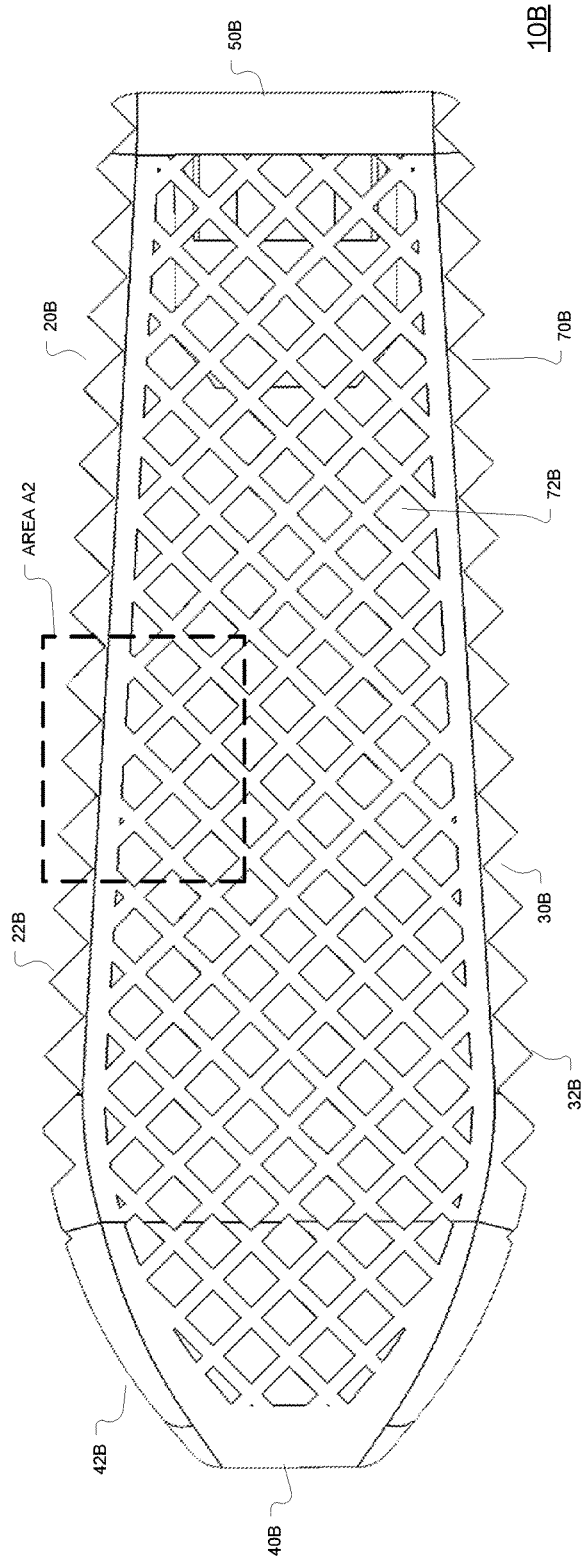
FIG. 2F is a simplified, left-side view of the bony interbody apparatus shown in FIG. 2A according to various embodiments.
Figure 2G:
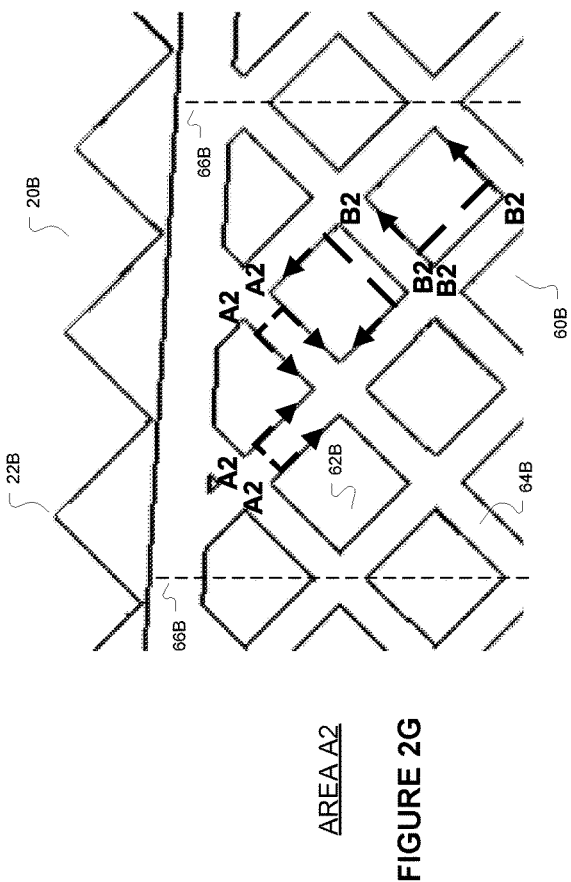
FIG. 2G is a simplified left-side view of area A2 of the bony interbody apparatus shown in FIG. 2F according to various embodiments.

FIG. 2A is a simplified, isometric left-side view of a bony interbody apparatus 10B according to various embodiments where the interbody may be a Transforaminal Straight Lumbar Interbody Fusion (TSLIF) interbody. FIG. 2B is a simplified, X-Y cross-sectional left-side view of the bony interbody apparatus 10B shown in FIG. 2A according to various embodiments. FIG. 2C is a simplified, X-Y cross-sectional top view of the bony interbody apparatus 10C shown in FIG. 2A according to various embodiments. FIG. 2D is a simplified, back view of the bony interbody apparatus 10D shown in FIG. 2A according to various embodiments. FIG. 2E is a simplified, front view of the bony interbody apparatus 10B shown in FIG. 2A according to various embodiments.

FIG. 2F is a simplified, left-side view of the bony interbody apparatus 10B shown in FIG. 2A according to various embodiments. FIG. 2G is a simplified left-side view of area A2 of the bony interbody apparatus 10B shown in FIG. 2F according to various embodiments. As shown in FIGS. 2A-2G, the interbody apparatus 10B includes a top 20B, bottom 30B, front 40B, back 50B, right-side 60B, and left-side 70B. The apparatus 10B includes a large central fenestration 24B extending completely from the top 20B to the bottom 30B. The apparatus also includes side fenestrations 62B, 44B that extend completely from its right-side 60B (and front area 40A) to the its left-side 70B matching fenestrations 72B. 44A (complete channels). As shown in FIGS. 2A-2G, the apparatus 10B may include a tool interface 52B with a threaded channel 54B sized to engage a tool and its screw.

As shown in the FIGS. 2A-2G and in detail in FIG. 2G, side fenestrations 62B, 72B, may also have walls 64B having a substantially uniform width A2-A2 that form the fenestrations 62B opening widths B2-B2. In an embodiment, the wall width A2-A2 may be about 0.15 to 0.5 mm and about 0.30 mm in an embodiment and the opening widths B2-B2 may be about 0.4 mm to 2.0 mm and about 0.80 mm in an embodiment.

As also shown in FIGS. 2A-2G and in particular in FIG. 2A, the apparatus 10B may have a substantially uniform upper surface and lower surface offset width C2-C2 and D2-D2 from the side fenestrations 44B, 62B, 72B. In an embodiment, the widths C2-C2 and D2-D2 may be about 0.5 mm to 3.0 mm and about 1.25 mm and 1.5 mm in an embodiment. It is noted that the apparatus 10B may also have a range of overall lengths of about 20 to 35 mm, widths of about 8 mm to 15 mm, and heights of about mm to 20 mm depending on the patient anatomy.

This uniform offset C2-C2, D2-D2 width, wall widths A2-A2, and opening widths B2-B2 may enable the apparatus 10B to support the loads created between the bony regions 222 without failure. The apparatus 10B further includes fenestrations 26B, 27B in its formed teeth or protrusions 22B that form complete channels to its bottom 30B teeth or protrusions 32B. These channels formed by the fenestrations 26B, 27B, 44B, 62B, 72B, as noted a) may prove scaffolds for bony growth and b) may provide pathways for imaging system signals.

Similar to implant 10A, in implant 10B the ratio of the wall width A2-A2 to the opening widths B2-B2 may be about 1:4 to 1:2 and about 3:8 in an embodiment. Further, a line 66B vertically bisecting the diamond pattern side fenestrations 62B may be oriented perpendicularly to the top and the bottom surfaces 20B, 30B to provide uniform load distribution to the sloped (for lordosis) surfaces 20B, 30B. In an embodiment as shown FIGS. 2A-2G, the front 40B insertion area including the slanted surface 42B may be stronger than the adjacent section of the implant 10B. As shown in FIGS. 2A-2G, the implant 10B insertion area 42B may not include vertical fenestrations 27B or be part of the large central fenestration 24B. Further, the insertion area 42B may not include teeth or protrusions 22B easing the insertion resistance and further strengthening the insertion area 42B. In addition, the rear 50B tool engagable shaped recess 52B and threaded section 54B may not include vertical fenestrations 27B and side fenestrations 62B.

Figure 3A:
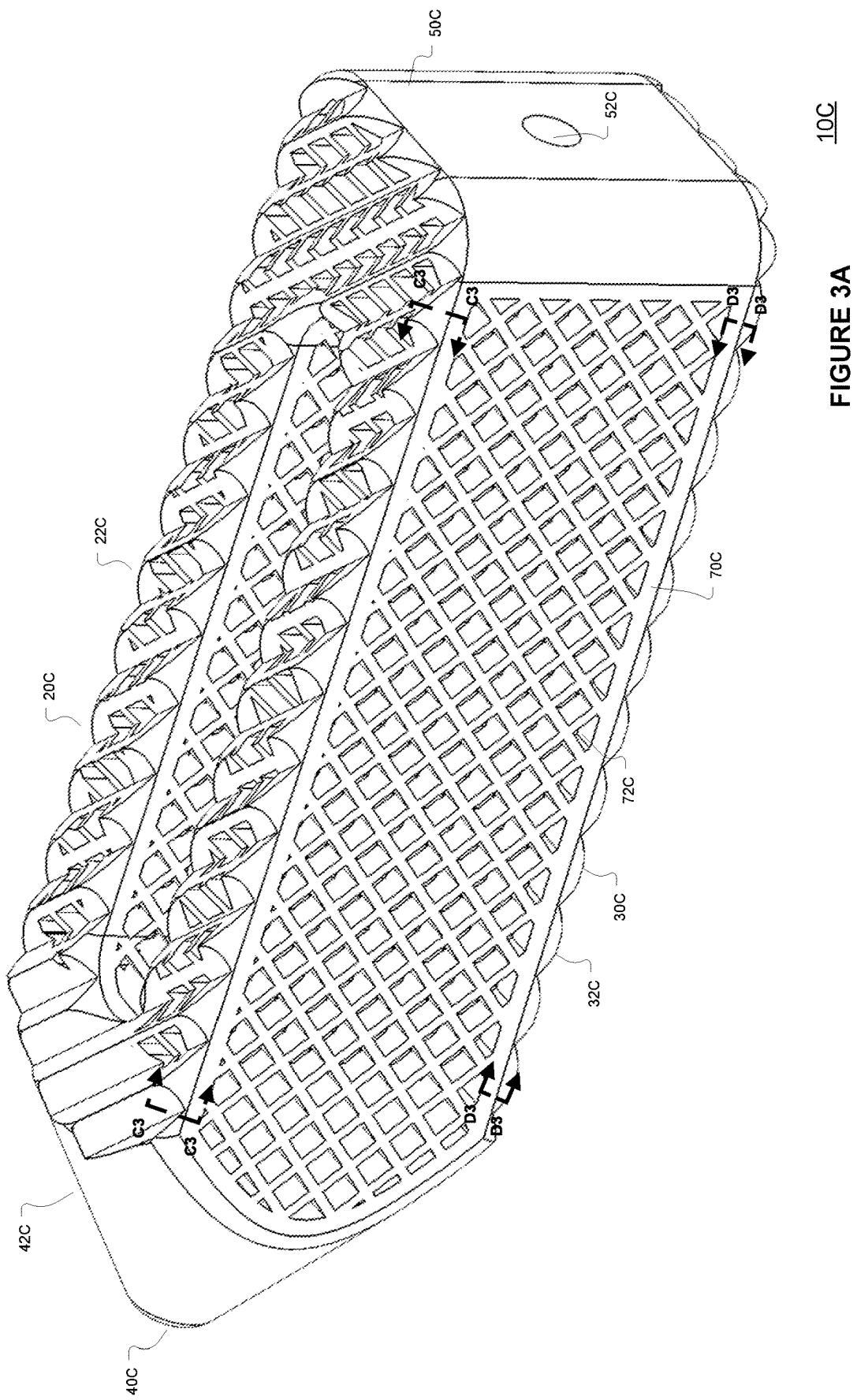
FIG. 3A is a simplified, isometric left-side view of a bony interbody apparatus according to various embodiments where the interbody may be an Oblique Lumbar Interbody Fusion (OLIF) interbody.
Figure 3B:
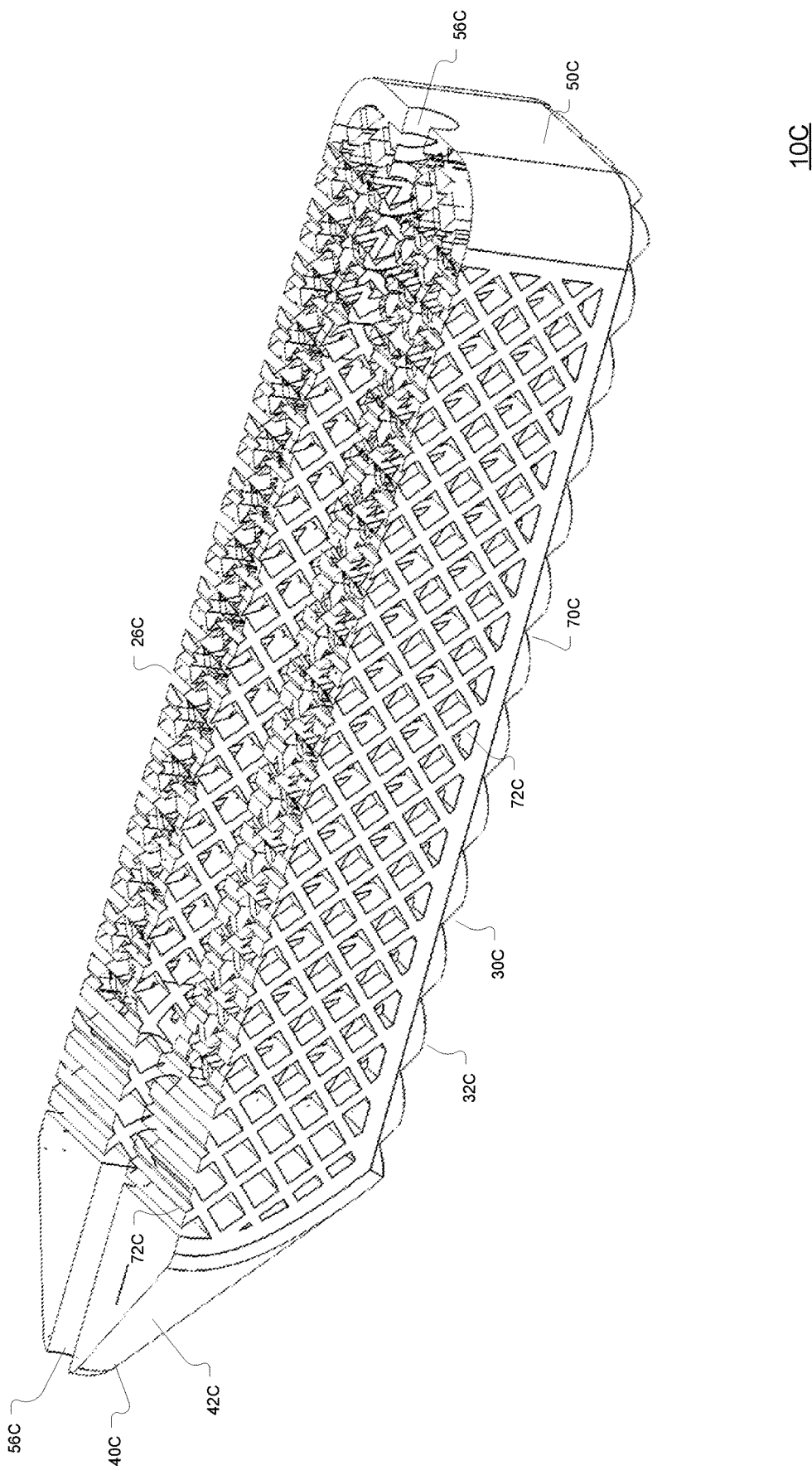
FIG. 3B is a simplified, X-Y cross-sectional left-side view of the bony interbody apparatus shown in FIG. 3A according to various embodiments.

FIG. 3A is a simplified, isometric left-side view of a bony interbody apparatus 10C according to various embodiments where the interbody may be an Oblique Lumbar Interbody Fusion (OLIF) interbody. FIG. 3B is a simplified, X-Y cross-sectional left-side view of the bony interbody apparatus 10C shown in FIG. 3A according to various embodiments. FIG. 3C is a simplified, X-Y cross-sectional top view of the bony interbody apparatus 10C shown in FIG. 3A according to various embodiments. FIG. 3D is a simplified, back view of the bony interbody apparatus 10C shown in FIG. 3A according to various embodiments.

FIG. 3E is a simplified, front view of the bony interbody apparatus 10C shown in FIG. 3A according to various embodiments. FIG. 3F is a simplified, left-side view of the bony interbody apparatus 10C shown in FIG. 3A according to various embodiments. FIG. 3G is a simplified left-side view of area A3 of the bony interbody apparatus 10C shown in FIG. 3F according to various embodiments. As shown in FIGS. 3A-3G, the interbody apparatus 10C includes a top 20C, bottom 30C, front 40C, back 50C, right-side 60C, and left-side 70C. The apparatus 10C includes a large central fenestration 24C extending completely from the top 20C to the bottom 30C. The apparatus also includes side fenestrations 62C that extend completely from its right-side 60C to the its left-side 70C matching fenestrations 72C (complete channels). As shown in FIG. 3B, the apparatus 10C may also include a central fenestration 56C forming a completed channel from the back 50C to the front 40C. The apparatus 10C may be inserted over a guide wire via the fenestration 56C in an embodiment.

As shown in the FIGS. 3A-3G and in detail in FIG. 3G, side fenestrations 62C, 72C, may also have walls 64C having a substantially uniform width A3-A3 that form the fenestrations 62C opening widths B3-B3. In an embodiment, the wall width A3-A3 may be about 0.15 to 0.5 mm and about 0.30 mm in an embodiment and the opening widths B3-B3 may be about 0.4 mm to 2.0 mm and about 0.80 mm in an embodiment.

As also shown in FIGS. 3A-3G and in particular in FIG. 3A, the apparatus 10C may have a substantially uniform upper surface and lower surface offset width C3-C3 and D3-D3 from the side fenestrations 62C, 72C. In an embodiment, the widths C3-C3 and D3-D3 may be about 0.5 mm to 3.0 mm and about 1.25 mm and 1.5 mm in an embodiment. It is noted that the apparatus 10C may also have a range of overall lengths of about 20 to 35 mm, widths of about 8 mm to 15 mm, and heights of about 7 mm to 20 mm depending on the patient anatomy.

This uniform offset C3-C3, D3-D3 width, wall widths A3-A3, and opening widths B3-B3 may enable the apparatus 10C to support the loads created between the bony regions 222 without failure. The apparatus 10C further includes fenestrations 26C, 27C in its formed teeth or protrusions 22C that form complete channels to its bottom 30C teeth or protrusions 32C. These channels formed by the fenestrations 26C, 27C, 62C, 72C, as noted a) may prove scaffolds for bony growth and b) may provide pathways for imaging system signals.

Similar to implants 10A and 10B, in implant 10C the ratio of the wall width A3-A3 to the opening widths B3-B3 may be about 1:4 to 1:2 and about 3:8 in an embodiment. Further, a line 66C vertically bisecting the diamond pattern side fenestrations 62C may be oriented perpendicularly to the top and the bottom surfaces 20C, 30C to provide uniform load distribution to the surfaces 20C, 30C. In an embodiment as shown FIGS. 3A-3G, the front 40C insertion area including the slanted and curved surface 42C may be stronger than the adjacent section of the implant 10C. As shown in FIGS. 3A-3G, the implant 10C insertion area 42C may not include vertical fenestrations 27C or be part of the large central fenestration 24C. Further, the insertion area 42C may not include teeth or protrusions 22C easing the insertion resistance and further strengthening the insertion area 42C. In addition, the rear 50C recess 52B may not include vertical fenestrations 27C and side fenestrations 62C.

Figure 4A:
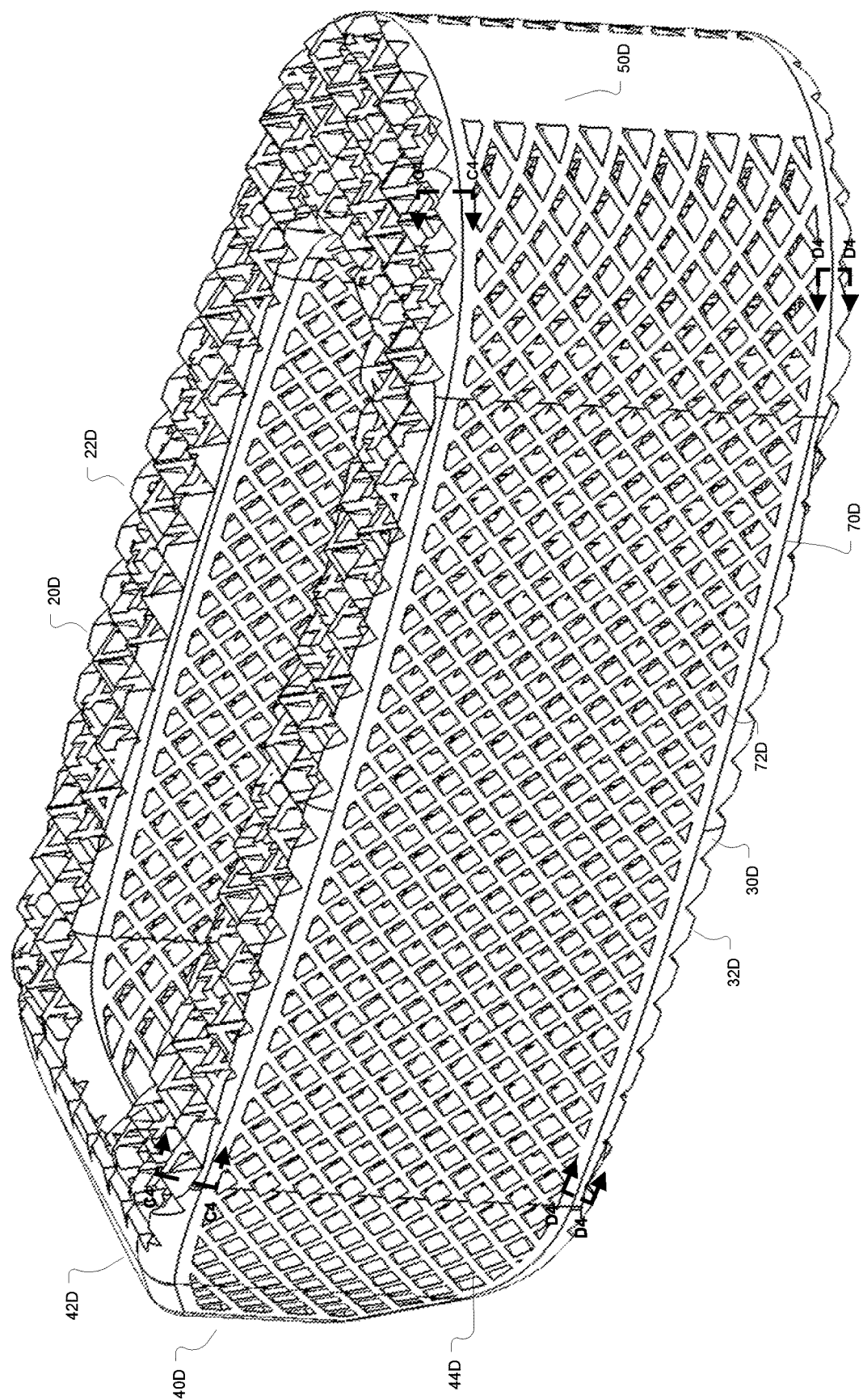
FIG. 4A is a simplified, isometric left-side view of a bony interbody apparatus according to various embodiments where the interbody may be a Lateral Lumbar Interbody Fusion (LLIF) interbody.

FIG. 4A is a simplified, isometric left-side view of a bony interbody apparatus 10D according to various embodiments where the interbody 10D may be a Lateral Lumbar Interbody Fusion (LLIF) interbody. FIG. 4B is a simplified, X-Y cross-sectional left-side view of the bony interbody apparatus 10D shown in FIG. 4A according to various embodiments. FIG. 4C is a simplified, X-Y cross-sectional top view of the bony interbody apparatus 10D shown in FIG. 4A according to various embodiments. FIG. 4D is a simplified, back view of the bony interbody apparatus 10D shown in FIG. 4A according to various embodiments. FIG. 4E is a simplified, front view of the bony interbody apparatus 10D shown in FIG. 4A according to various embodiments.

Figure 4F:
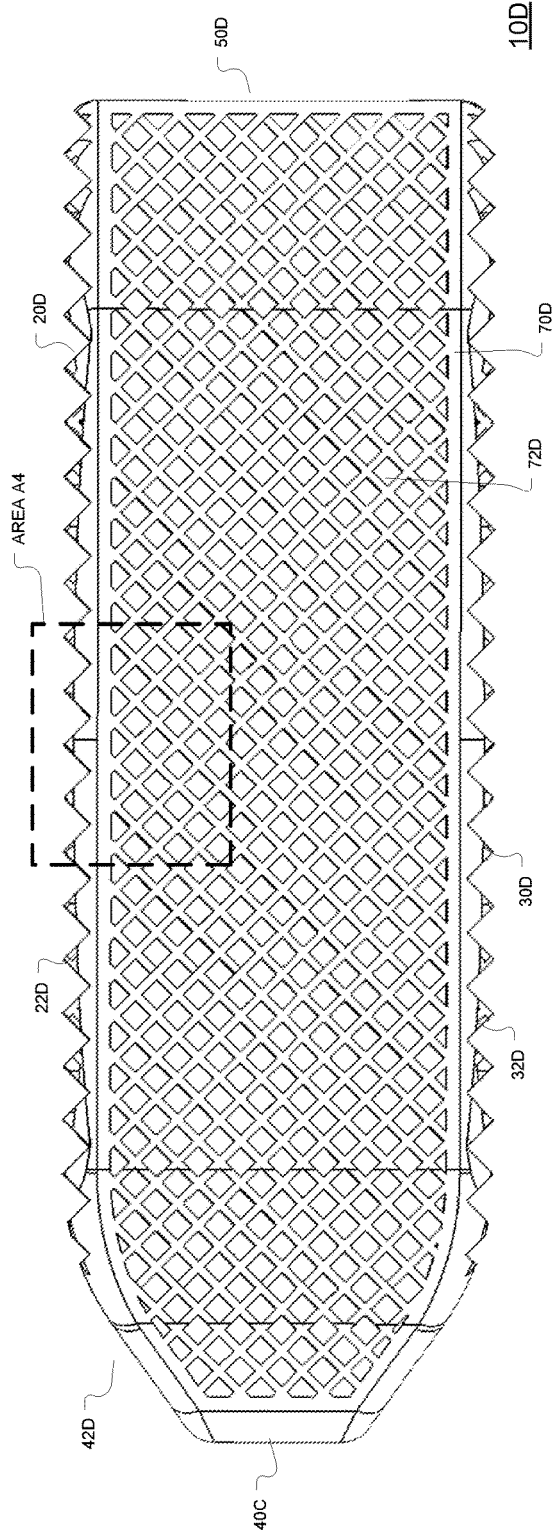
FIG. 4F is a simplified, left-side view of the bony interbody apparatus shown in FIG. 4A according to various embodiments.
Figure 4G:
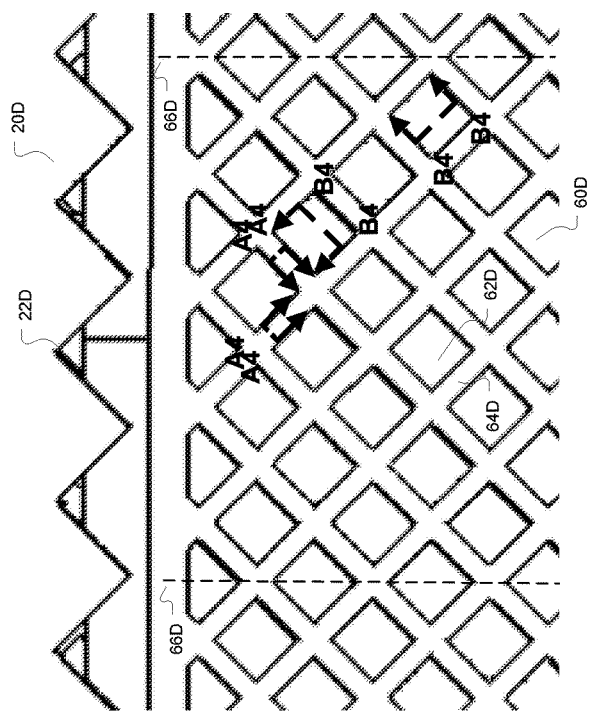
FIG. 4G is a simplified left-side view of area A4 of the bony interbody apparatus shown in FIG. 4F according to various embodiments.

FIG. 4F is a simplified, left-side view of the bony interbody apparatus 10D shown in FIG. 4A according to various embodiments. FIG. 4G is a simplified left-side view of area A4 of the bony interbody apparatus 10D shown in FIG. 4F according to various embodiments. As shown in FIGS. 4A-4G, the interbody apparatus 10D includes a top 20D, bottom 30D, front 40D, back 50D, right-side 60D, and left-side 70D. The apparatus 10D includes a large central fenestration 24D extending completely from the top 20D to the bottom 30D. The apparatus also includes side fenestrations 43D, 53D, 62D that extend completely from its right-side 60D to the its left-side 70D matching fenestrations 43D, 53D, 72D (complete channels).

As shown in the FIGS. 4A-4G and in detail in FIG. 4G, side fenestrations 62D, 72D, may also have walls 64D having a substantially uniform width A4-A4 that form the fenestrations 62D opening widths B4-B4. In an embodiment, the wall width A4-A4 may be about 0.15 to 0.5 mm and about 0.30 mm in an embodiment and the opening widths B4-B4 may be about 0.4 mm to 2.0 mm and about 0.80 mm in an embodiment.

As also shown in FIGS. 4A-4G and in particular in FIG. 4A, the apparatus 10D may have a substantially uniform upper surface and lower surface offset width C4-C4 and D4-D4 from the side fenestrations 62D, 72D. In an embodiment, the widths C4-C4 and D4-D4 may be about 0.5 mm to 3.0 mm and about 1.25 mm and 1.5 mm in an embodiment. It is noted that the apparatus 10D may also have a range of overall lengths of about 20 to 60 mm, widths of about 8 mm to 25 mm, and heights of about 7 mm to 20 mm depending on the patient anatomy.

This uniform offset C4-C4, D4-D4 width, wall widths A4-A4, and opening widths B4-B4 may enable the apparatus 10D to support the loads created between the bony regions 222 without failure. The apparatus 10D further includes fenestrations 26D, 27D in its formed teeth or protrusions 22D that form complete channels to its bottom 30D teeth or protrusions 32D. These channels formed by the fenestrations 26D, 27D, 43D, 53D, 62D, 72D, as noted a) may prove scaffolds for bony growth and b) may provide pathways for imaging system signals.

The ratio of the wall width A4-A4 to the opening widths B4-B4 may be about 1:4 to 1:2 and about 3:8 in an embodiment. Further, a line 66D vertically bisecting the diamond pattern side fenestrations 62D may be oriented perpendicularly to the top and the bottom surfaces 20D, 30D to provide uniform load distribution across the surfaces 20D, 30D. In an embodiment as shown FIGS. 4A-4G, the front 40D insertion area including the slanted surface 42D may be stronger than the adjacent section of the implant 10D. As shown in FIGS. 4A-4G, the implant 10D insertion area 42D may not include vertical fenestrations 27D or be part of the large central fenestration 24D. Further, the insertion area 42D may not include teeth or protrusions 22D easing the insertion resistance and further strengthening the insertion area 42D.

Figure 5A:
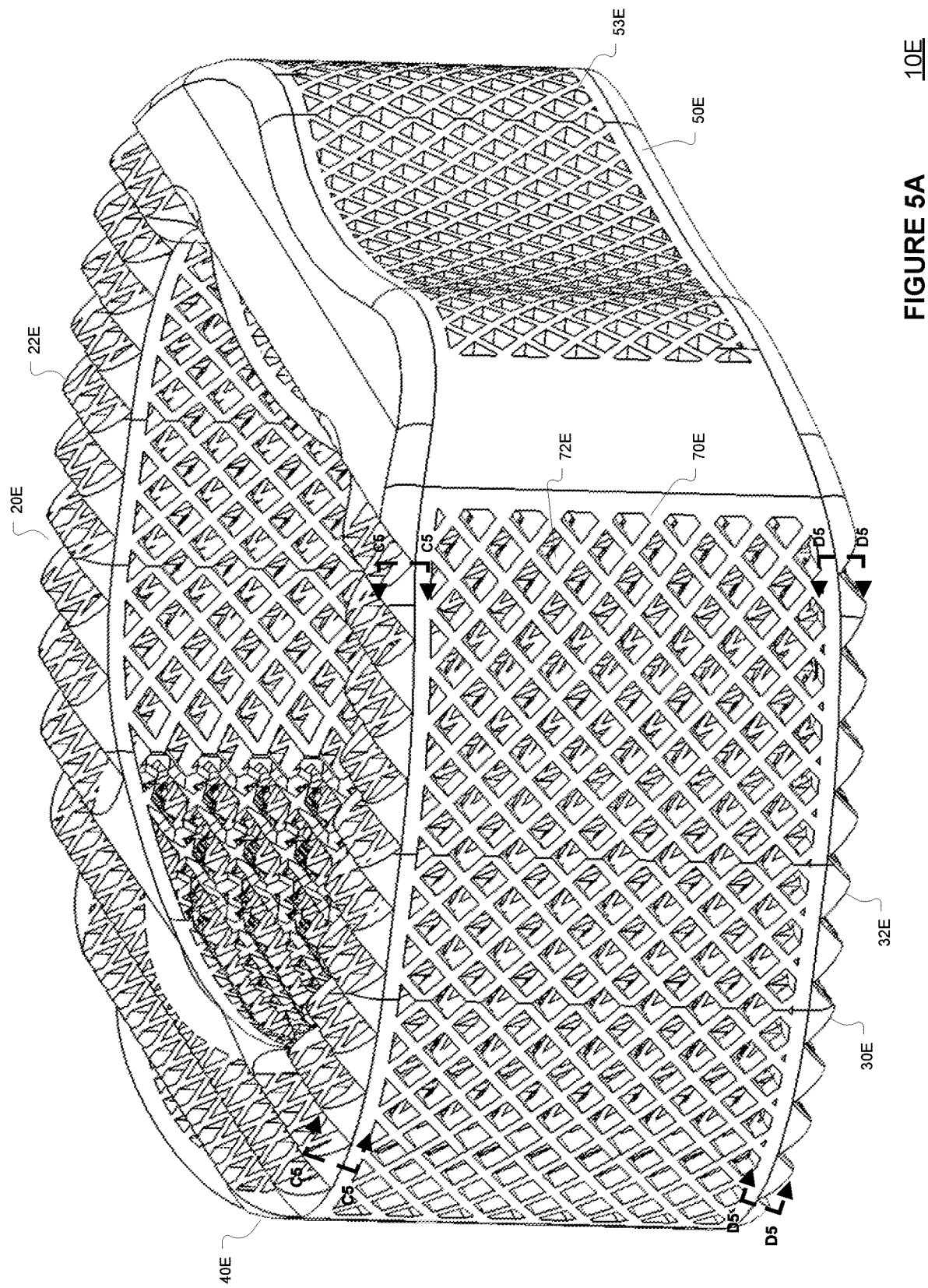
FIG. 5A is a simplified, isometric left-side view of a bony interbody apparatus according to various embodiments where the interbody may be an Anterior Lumbar Interbody Fusion (ALIF) interbody.
Figure 5B:
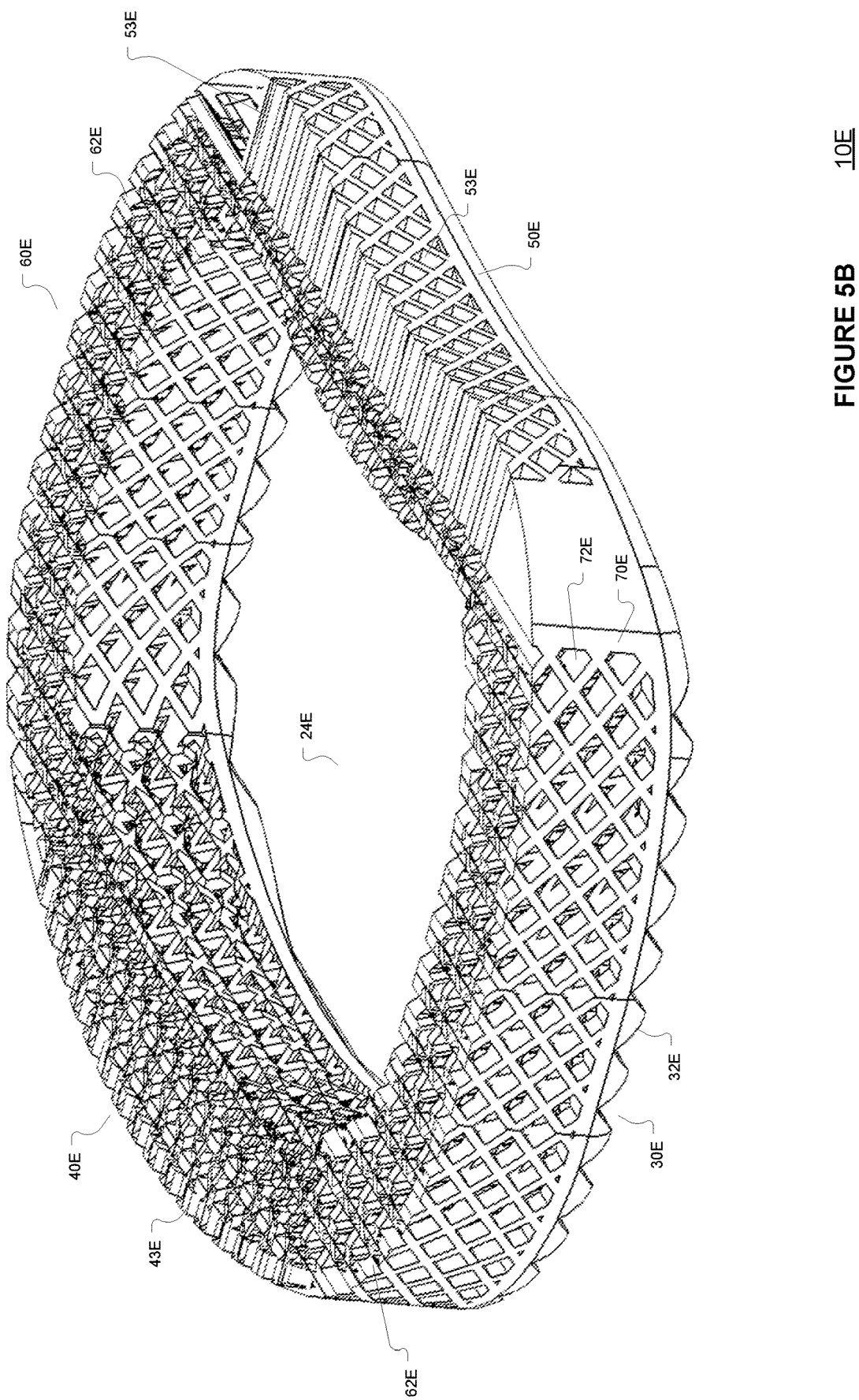
FIG. 5B is a simplified, X-Y cross-sectional left-side view of the bony interbody apparatus shown in FIG. 5A according to various embodiments.
Figure 5C:
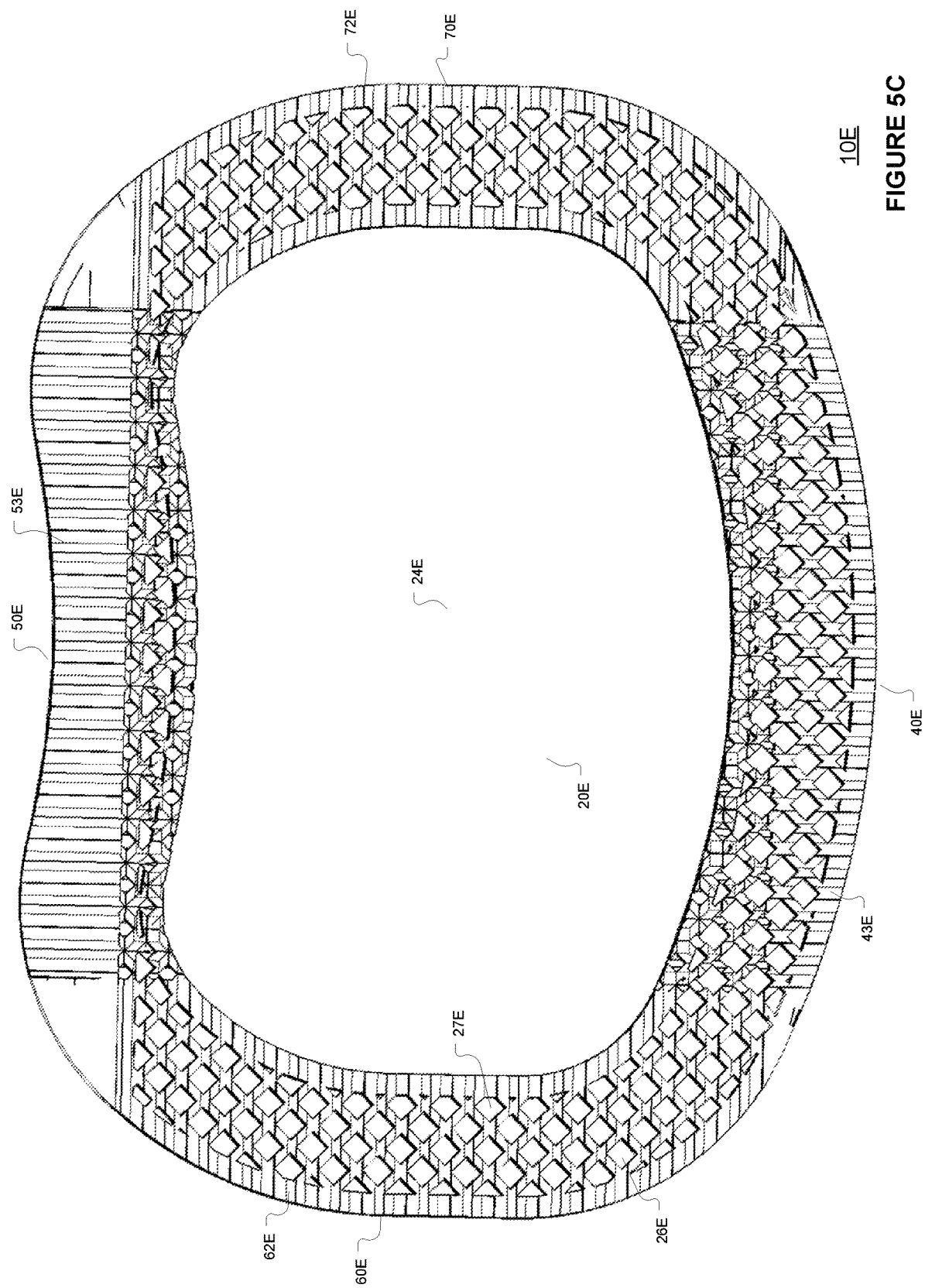
FIG. 5C is a simplified, X-Y cross-sectional top view of the bony interbody apparatus shown in FIG. 5A according to various embodiments.

FIG. 5A is a simplified, isometric left-side view of a bony interbody apparatus 10E according to various embodiments where the interbody 10E may be an Anterior Lumbar Interbody Fusion (ALIF) interbody. FIG. 5B is a simplified, X-Y cross-sectional left-side view of the bony interbody apparatus 10E shown in FIG. 5A according to various embodiments. FIG. 5C is a simplified, X-Y cross-sectional top view of the bony interbody apparatus 10E shown in FIG. 5A according to various embodiments. FIG. 5D is a simplified, back view of the bony interbody apparatus 10E shown in FIG. 5A according to various embodiments.

FIG. 5E is a simplified, front view of the bony interbody apparatus 10E shown in FIG. 5A according to various embodiments. FIG. 5F is a simplified, left-side view of the bony interbody apparatus 10E shown in FIG. 5A according to various embodiments. FIG. 5G is a simplified left-side view of area A5 of the bony interbody apparatus 10E shown in FIG. 5F according to various embodiments. As shown in FIGS. 5A-5G, the interbody apparatus 10E includes a top 20E, bottom 30E, front 40E, back 50E, right-side 60E, and left-side 70E. The apparatus 10E includes a large central fenestration 24E extending completely from the top 20E to the bottom 30E. The apparatus also includes side fenestrations 43E, 53E, 62E that extend completely from its right-side 60E to the its left-side 70E matching fenestrations 43E, 53E, 72E (complete channels).

As shown in the FIGS. 5A-5G and in detail in FIG. 5G, side fenestrations 62E, 72E, may also have walls 64E having a substantially uniform width A5-A5 that form the fenestrations 62E opening widths B5-B5. In an embodiment, the wall width A5-A5 may be about 0.15 to 0.5 mm and about 0.30 mm in an embodiment and the opening widths B5-B5 may be about 0.4 mm to 2.0 mm and about 0.80 mm in an embodiment.

As also shown in FIGS. 5A-5G and in particular in FIG. 5A, the apparatus 10e may have a substantially uniform upper surface and lower surface offset width C5-C5 and D5-D5 from the side fenestrations 62E, 72E. In an embodiment, the widths C5-C5 and D5-D5 may be about 0.5 mm to 3.0 mm and about 1.25 mm and 1.5 mm in an embodiment. It is noted that the apparatus 10E may also have a range of overall lengths of about 20 to 60 mm, widths of about 8 mm to 25 mm, and heights of about 7 mm to 20 mm depending on the patient anatomy.

This uniform offset C5-C5, D5-D5 width, wall widths A5-A5, and opening widths B5-B5 may enable the apparatus 10D to support the loads created between the bony regions 222 without failure. The apparatus 10E further includes fenestrations 26E, 27E in its formed teeth or protrusions 22E that form complete channels to its bottom 30E teeth or protrusions 32E. These channels formed by the fenestrations 26E, 27E, 43E, 53E, 62E, 72E, as noted a) may prove scaffolds for bony growth and b) may provide pathways for imaging system signals.

In implant 10E the ratio of the wall width A5-A5 to the opening widths B5-B5 may be about 1:4 to 1:2 and about 3:8 in an embodiment. Further, a line 66E vertically bisecting the diamond pattern side fenestrations 62E may be oriented perpendicularly to the top and the bottom surfaces 20E, 30E to provide uniform load distribution to the surfaces 20E, 30E. In an embodiment as shown FIGS. 5A-5G, the rear 50E area may be stronger than the adjacent section of the implant 10E. As shown in FIGS. 5A-5G, the implant 10E rear 50E area may not include vertical fenestrations 27E or be part of the large central fenestration 24E. Further, the insertion area 42E may not include teeth or protrusions 22E easing the insertion resistance and further strengthening the rear area 50E. In addition, the rear 50C recess 52B may not include vertical fenestrations 27C and side fenestrations 62C.

Figure 6B:
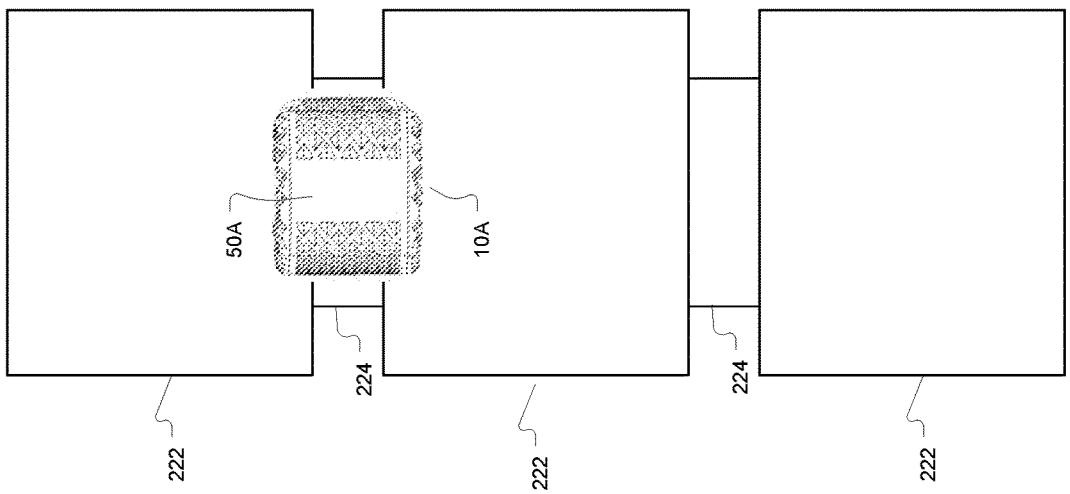
FIG. 6B is a simplified, back view of the interbody shown in FIGS. 1A-1H inserted between two adjacent bony segments according to various embodiments.
Figure 6A:
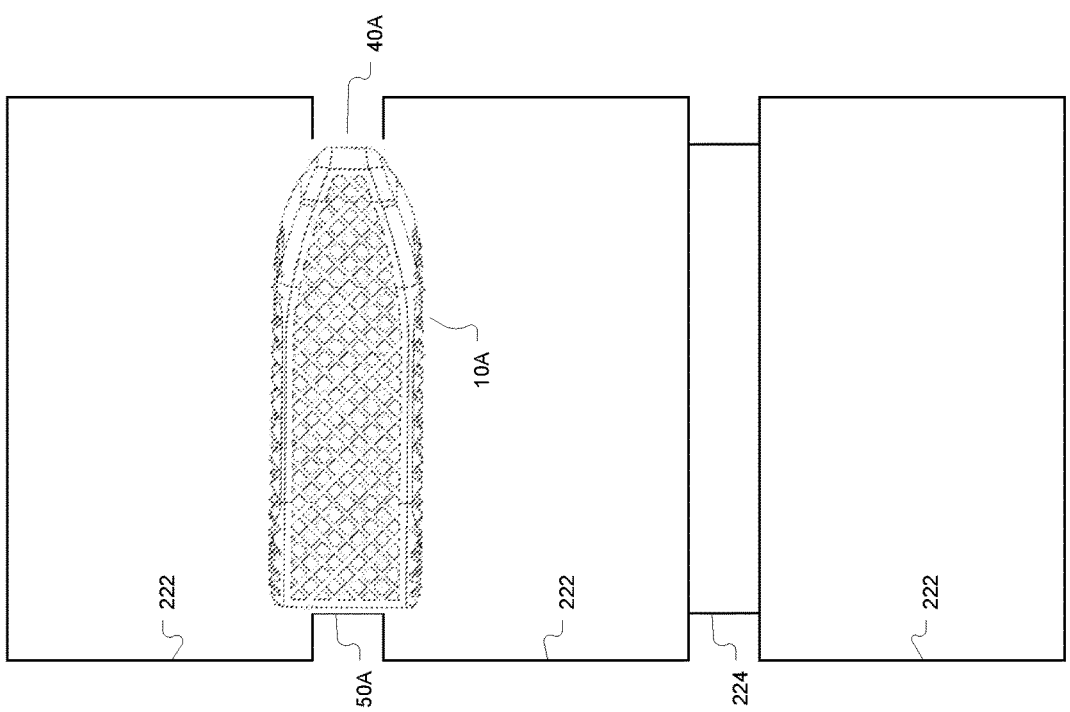
FIG. 6A is a simplified, right view of the interbody shown in FIGS. 1A-1H inserted between two adjacent bony segments according to various embodiments.

It is noted that any of the interbodies 10A-10E may have sloped top and bottom surfaces 20A-20E, 30A-30E for lordotic support where the slopes may vary from 0 degrees to 13 degrees in an embodiment. FIG. 6A is a simplified, right view of the interbody 10A shown in FIGS. 1A-1H inserted between two adjacent bony segments according to various embodiments. FIG. 6B is a simplified, back view of the interbody 10A shown in FIGS. 1A-1H inserted between two adjacent bony segments according to various embodiments. In an embodiment, the large central fenestrations 24A-24E extending from the implants 10A-10E top surface 20A-20E to bottom surface 30A-30E may comprise 30 to 85% of the surfaces 20A-20E, 30A-30E enabling a large volume of bony matrix to be inserted therein if desired and increasing visibility via imaging. In implants 10A-E the ratio of the wall widths between fenestrations 26A-E and 27A-E to the fenestrations 26A-E and 27A-E opening widths may be about 1:4 to 1:2 and about 3:8 in an embodiment.

The accompanying drawings that form a part hereof show, by way of illustration and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In the foregoing Detailed Description, various features are grouped together in a single embodiment for the purpose of streamlining the disclosure. This method of disclosure is not to be interpreted to require more features than are expressly recited in each claim. Rather, inventive subject matter may be found in less than all features of a single disclosed embodiment. Thus the following claims are hereby incorporated into the Detailed Description, with each claim standing on its own as a separate embodiment.

What is claimed is:

1. A metal-alloy based interbody for placement between two, adjacent bony mammalian regions, the interbody including:
   a top side including a surface configured to engage one of the two, adjacent bony mammalian regions;
   a bottom side include a surface configured to engage the other of the two, adjacent bony mammalian regions;
   a left side including a surface;
   a right side including a surface;
   a front including a surface;
   a back including a surface;
   a central fenestration extending from the top side surface to the bottom side surface and comprising 30 to 85% of the top side surface and the bottom side surface; and
   a first plurality of fenestrations extending from the top side surface to the bottom side surface for a first majority of the top side surface from the front surface to the back surface of the interbody other than the central fenestration, each of the first plurality of fenestrations opening having a width and the distance between walls of adjacent first plurality of fenestrations having a length that is two to four times less than the first plurality of fenestrations opening width; and
   a second plurality of fenestrations extending from the left side surface to the right surface for a second majority of the left side including a surface from the front surface to back surface of the interbody other than the central fenestration, each of the second plurality of fenestrations opening having a width and the distance between walls of adjacent second plurality of fenestrations having a length that is two to four times less than the second plurality of fenestrations opening width, wherein the second majority is greater than the first majority and a plurality of the second plurality of fenestrations do not intersect with each other via other fenestrations.

2. The metal-alloy based interbody system of claim 1, wherein the second plurality of fenestrations extend further to one of the front surface and back surface of the interbody than the first plurality of fenestrations.

3. The metal-alloy based interbody system of claim 2, the top side surface includes protrusions configured to engage the one of the two, adjacent bony mammalian regions and the bottom side surface includes protrusions configured to engage the one of the two, adjacent bony mammalian regions.

4. The metal-alloy based interbody system of claim 3, wherein a majority of the openings formed by each of the second plurality of fenestrations are diamond shaped.

5. The metal-alloy based interbody system of claim 4, wherein a majority of the openings formed by each of the first plurality of fenestrations are diamond shaped.

6. The metal-alloy based interbody system of claim 5, wherein a majority of the openings formed by each of the second plurality of fenestrations are diamond shaped with one of the diamond tips of each of the plurality of second fenestrations is oriented to a normal surface of the top side surface.

7. The metal-alloy based interbody system of claim 6, wherein the width of each of the second plurality of fenestrations openings is from 0.4 mm to 2.0 mm.

8. The metal-alloy based interbody system of claim 7, wherein walls between adjacent second plurality of fenestrations have a length of from 0.15 to 0.5 mm.

9. The metal-alloy based interbody system of claim 2, wherein a section of the top side surface extending towards one of the front side and the back side does not include any of the first plurality of fenestrations.

10. The metal-alloy based interbody system of claim 9, wherein a section of the top side surface towards the other of the one of the front side and the back side does not include any of the first plurality of fenestrations.

11. The metal-alloy based interbody system of claim 1, wherein each of the first plurality of fenestrations intersect with one of the second plurality of fenestrations.

12. The metal-alloy based interbody system of claim 11, wherein walls between adjacent second plurality of fenestrations have a length of from 0.15 to 0.5 mm.

13. The metal-alloy based interbody system of claim 12, wherein the width of each of the second plurality of fenestrations openings is from 0.4 mm to 2.0 mm.

14. The metal-alloy based interbody system of claim 12, wherein walls between adjacent first plurality of fenestrations have a length of from 0.15 to 0.5 mm.

15. The metal-alloy based interbody system of claim 14, wherein the width of each of the first plurality of fenestrations openings is from 0.4 mm to 2.0 mm.

16. The metal-alloy based interbody system of claim 1, wherein a majority of the openings formed by each of the second plurality of fenestrations are diamond shaped.

17. The metal-alloy based interbody system of claim 16, wherein a majority of the openings formed by each of the first plurality of fenestrations are diamond shaped.

18. The metal-alloy based interbody system of claim 17, wherein a majority of the openings formed by each of the second plurality of fenestrations are diamond shaped with one of the diamond tips of each of the plurality of second fenestrations is oriented to a normal surface of the top surface.

19. The metal-alloy based interbody system of claim 1, wherein interbody is formed primarily of titanium.

20. The metal-alloy based interbody system of claim 1, wherein interbody is formed primarily of titanium via an additive printing process.

* * * * *